United States Patent [19]

Ahlem et al.

[11] Patent Number: 5,273,743

[45] Date of Patent: Dec. 28, 1993

[54] TRIFUNCTIONAL ANTIBODY-LIKE COMPOUNDS AS A COMBINED DIAGNOSTIC AND THERAPEUTIC AGENT

[75] Inventors: Clarence Ahlem, San Diego; Ann E. Huang, Carlsbad, both of Calif.

[73] Assignee: Hybritech Incorporated, San Diego, Calif.

[21] Appl. No.: 808,193

[22] Filed: Dec. 13, 1991

Related U.S. Application Data

[62] Division of Ser. No. 491,406, Mar. 9, 1990, abandoned.

[51] Int. Cl.$^5$ ............... A61K 39/395; A61K 39/44; A61K 49/02; C07K 15/28
[52] U.S. Cl. ..................... 424/85.8; 424/1.1; 424/9; 424/85.91; 530/387.3; 530/388.2; 530/388.85; 530/388.9; 530/391.5; 530/391.7; 530/391.9; 530/389.7; 530/389.8; 530/391.1; 530/391.3; 435/972; 436/819
[58] Field of Search .................. 424/85.8, 85.91, 1.1, 424/9; 530/387.3, 388.2, 389.7, 391.1, 391.3, 391.5, 391.7, 391.9, 388.85, 388.9, 389.8; 436/819; 435/972

[56] References Cited

U.S. PATENT DOCUMENTS

| | | | |
|---|---|---|---|
| 3,927,193 | 12/1975 | Hansen et al. | 424/1.1 |
| 4,433,059 | 2/1984 | Chang et al. | 436/512 |
| 4,659,839 | 4/1987 | Nicolotti et al. | 548/546 |
| 4,671,958 | 6/1987 | Rodwell et al. | 424/85.91 |
| 4,676,980 | 6/1987 | Segal et al. | 424/88 |
| 4,687,732 | 8/1987 | Ward et al. | 435/6 |
| 4,714,681 | 12/1987 | Reading et al. | 435/240.27 |
| 4,722,892 | 2/1988 | Meares et al. | 435/7 |
| 4,814,438 | 3/1989 | Armour et al. | 536/23 |
| 4,831,122 | 5/1989 | Buchsbaum | 424/1.1 |
| 4,837,003 | 6/1989 | Nicolotti et al. | 424/1.1 |
| 5,091,542 | 2/1992 | Ahlem et al. | 548/521 |

FOREIGN PATENT DOCUMENTS

| | | | |
|---|---|---|---|
| 0088695 | 9/1983 | European Pat. Off. | 33/54 |
| 0134041 | 3/1985 | European Pat. Off. | |
| 0217577 | 4/1987 | European Pat. Off. | |
| 220137 | 4/1987 | European Pat. Off. | |

(List continued on next page.)

OTHER PUBLICATIONS

Liu et al. (1985) PNAS USA 82:8648–8652.
Tutt et al. (1991) J. Immunol 147(1)60–69.
Jung et al. (1991) Eur. J. Immunol. 21:2431–2435.
Glennie et al. (1987) J. Immunol. 139:2367–2375.

(List continued on next page.)

Primary Examiner—Kay K. Kim
Attorney, Agent, or Firm—Paul C. Steinhardt; June M. Bostich; Donald J. Pochopien

[57] ABSTRACT

The present invention has multiple aspects. In its first aspect the present invention is directed to a trifunctional antibody-like compound that has tissue, organ, cell or molecule specificity and which is capable of being bifunctional when immobilized, via binding, at the tissue, organ, cell or molecule for which it has specificity. In particular, the present invention is directed to a trifunctional antibody-like compound of Formula I:

$$F_1ab'-L-F_2ab'-L-F_3ab' \qquad (1)$$

wherein L is the same or two different moieties for cross-linking $F_1ab'$, $F_2ab'$ and $F_3ab'$;

wherein $F_1ab'$ is an Fab'-like fragment of a polyclonal or monoclonal antibody having specificity for an antigen expressed by the organ, tissue, cell or molecule of interest;

wherein $F_2ab'$ is an Fab'-like fragment of a polyclonal or monoclonal antibody having the same specificity as $F_1ab'$, or having specificity either for a different antigen expressed by the organ, tissue, cell, or molecule of interest, or for a diagnostic or therapeutic agent; and wherein $F_3ab'$ is an Fab'-like fragment of a polyclonal or monoclonal antibody having specificity for a diagnostic or therapeutic agent; or wherein $F_2ab'$ and $F_3ab'$ have specificity for a receptor/receptor complex and accessory molecule on the surface of a T-cell.

The compound of the present invention has utility as a pharmaceutical agent. Various methods for treating and diagnosing a disease are also presented.

26 Claims, No Drawings

FOREIGN PATENT DOCUMENTS

| | | |
|---|---|---|
| 0263046 | 4/1988 | European Pat. Off. . |
| 0272891 | 6/1988 | European Pat. Off. ............ 39/395 |
| 0329481 | 8/1989 | European Pat. Off. . |
| 0336379 | 10/1989 | European Pat. Off. ............ 39/395 |
| WO89/11863 | 12/1989 | PCT Int'l Appl. .................. 39/395 |
| WO90/04413 | 5/1990 | PCT Int'l Appl. .................. 39/395 |
| 2018250 | 10/1979 | United Kingdom . |
| 8601407 | 3/1986 | World Int. Prop. O. . |

OTHER PUBLICATIONS

*Chemical Dictionary* fifth edition, Grant et al. McGraw-Hill Book Company, N.Y. etc. 1987 p. 192.

Mashuo et al., "Cytoxicity of a Hybrid Prepared by Coupling Diphtheria Toxin A-chain with N,N'-o-phenylenedimaleimide," Biochem. and Biophys. Res. Comm. 102, 561–567 (1981).

Hashida, et al., "More Useful Maleimide Compounds for the Confugation of Fab' to Horseradish Peroxidase Though Thiol Groups in the Hinge," J. Appl. Biochem., 6, 56–63 (1984).

Hamaguchi, et al., "Improved Procedure for the Conjugation of Rabbit IgG and Fab' antibodies . . . , " J. Biochem, 85, 1289–1300 (1979).

Keller, et al., "Preparation and Some Properties of Maleimide Acids and Maleoyl Derivatives of Peptides," Helv. Chim. Acta, 58 531–541 (1975).

Beidler, et al., "Cloning and High Level Expression of a Chimeric Antibody with Specificity for Human Carcinoembryonic Antigen," J. Immunol., 141, 4053–60 (1988).

Reardan, et al., Antibodies Against Metal Chelates, Nature, 316, 265–268 (1985).

Stevenson et al. (1985a) "Surface Immunoglobulen of B-tumors as a therapeutic target" Cancer Surveys 4(1):213–244.

Stevenson et al. (1985b) "Preparation and properties of FabIg G . . . " Bioscience, Reports 5:992–998.

CA 107(20):176632F.

CA 111(6): 39963b.

Rich et al. (1975) J. Medicinal Chem. 18(10)1004–1010 (See p. 1006).

TRIFUNCTIONAL ANTIBODY-LIKE COMPOUNDS AS A COMBINED DIAGNOSTIC AND THERAPEUTIC AGENT

This invention is a division of Ser. No. 07/491,406, filed on Mar. 9, 1990 and now abandoned.

BACKGROUND OF THE INVENTION

The present invention is directed to a pharmaceutical composition comprising a trifunctional antibody-like compound for use in diagnostics and/or therapeutics. More specifically, the present invention is directed to a trifunctional antibody-like compound comprising three Fab'-like fragments having from 2-3 differing specificities (functions). In the trifunctional antibody-like compound, the first Fab' fragment is directed toward an antigen or antigenic site which confers tissue, organ, or tumor specificity to the compound. The remaining two Fab'-like fragments have specificities directed to a diagnostic and/or therapeutic agent or a combination thereof, or to the T-cell receptor/receptor complex and accessory molecule on the T-cell surface. The compound of the present invention is useful as a pharmaceutical agent that binds to one or more target bearing cells and which enables a treating physician to both image the target cells and to selectively treat a disease associated with the imaged target cell or cells; or it can bind to a target cell and localize a combination of therapeutic agents in proximity to the target cell or cells; or it can bindingly activate a T-cell to kill the target bearing cell for which it also has specificity.

Antibodies are complex protein molecules generated by an organism's immune system in response to an antigen perceived by the host as being foreign. The extreme plasticity and diversity of an animal's immune repertoire permits the generation of an enormous variety of antibody molecules to an equally large number of antigens. A problem with individual antibody molecules is that they are monospecific and therefore monofunctional.

The natural affinity of antibody molecules for their target antigens has been exploited for the in vivo targeting of an individual pharmacological composition, such as cytotoxic molecules, radionuclides, imaging agents, or other reporter groups, to specific antigenic sites on tumors, etiologic agents of infectious diseases and other antigen bearing entities. For example, Nicolotti and Dean (U.S. Pat. No. 4,659,839) describe a pharmaceutical composition consisting of an Fab' fragment cross-linked to a metal chelating agent. In Nicolotti, the Fab', which is directed to the carcinoembronyic antigen, is covalently bound to a metal chelating agent that is capable of chelating a radionuclide or paramagnetic metal ion.

Meares (U.S. Pat. No. 4,722,892) describes a pharmaceutical composition composed of a bifunctional antibody wherein one portion of the bifunctional molecule confers tumor (i.e. tissue) specificity, whereas the second portion confers specificity to a metal-chelate complex.

U.S. Pat. No. 4,814,438 (Armour et al.) describes the cross-linking of an antibody molecule to a group of 2'-2'-difluoronucleosides via an alkane dioic acid linking group. The antibody's sole function is to confer tissue specificity. Likewise, U.S. Pat. No. 4,671,958 (Rodwell et al.) discloses the use of antibody conjugates to deliver compounds to in vitro target sites. In Rodwell, the antibody confers tissue specificity. Peptide linker groups covalently bind the antibody to the compound of interest via amide or ester linkages. Because Rodwell uses intact antibody molecules, the immobilized antibodies also can activate complement. Rodwell teaches that complement activation can be used to enzymatically cleave the peptide linker causing the localized release of the pharmaceutical agent. However, an object of the present invention is to provide a pharmaceutical agent having the antigen binding capability of an antibody but which does not activate complement nor interact with Fc receptor bearing cells.

Notwithstanding the bifunctional nature of the antibody reagents described above, these bifunctional antibody molecules have the inherent limitation of effectively being monofunctional at the site of action, i.e., targeting only a single drug or reporter group to the antigen binding site on a tumor or other antigen bearing entity. Accordingly, another object of the present invention is to develop a pharmaceutical composition having tissue or organ specificity that will be bifunctional at the site of action.

A further object of the present invention is to develop a pharmaceutical composition having tissue or organ specificity that will permit both diagnosis and treatment.

SUMMARY OF THE INVENTION

The present invention has multiple aspects. In its first aspect the present invention is directed to a compound that has tissue, organ, cell, tumor, or molecule specificity and which is capable of being bifunctional when immobilized, via binding, at the tissue, organ, cell, tumor, or molecule for which it has specificity. In particular, the present invention is directed to a trifunctional antibody-like compound of Formula I:

$$F_1ab'—L—F_2ab'—L—F_3ab' \qquad (I)$$

wherein L is the same or two different moieties for covalently cross-linking $F_1ab'$, $F_2ab'$ and $F_3ab'$;

wherein $F_1ab'$ is an Fab'-like fragment of a polyclonal or monoclonal antibody having specificity for an antigen expressed by the organ, tissue, cell, tumor, or molecule of interest;

wherein $F_2ab'$ is an Fab'-like fragment of a polyclonal or monoclonal antibody having the same specificity as $F_1ab'$, or having specificity either for a different antigen expressed by the organ, tissue, cell, tumor, or molecule of interest, or for a diagnostic or therapeutic agent; and wherein $F_3ab'$ is an Fab'-like fragment of a polyclonal or monoclonal antibody having specificity for a diagnostic or therapeutic agent; or wherein $F_2ab'$ and $F_3ab'$ have specificity for a receptor/receptor complex and accessory molecule respectively on the surface of a T-cell.

In its second aspect the present invention is directed to a pharmaceutical composition comprising:

(a) the trifunctional antibody-like compound of Formula I; and (b) one or more pharmaceutically acceptable carriers.

In its third aspect, the present invention is directed to a method for diagnosing a disease, medical condition or biological status in a mammalian patient, preferably a human, comprising:

i. administering to the patient in need of diagnosis a diagnostically effective amount of a pharmaceutical agent comprising the compound of Formula I and one or more pharmaceutically acceptable carriers, said compound having at least one Fab'-like moiety with specificity for the organ, tissue, cell, or tumor about which a diagnosis is sought, said compound also having at least one Fab'-like moiety with specificity for an imaging agent; and ii. administering to the patient in need of diagnosis a diagnostically effective amount of an imaging agent, whereby the diagnosis of a disease, medical condition or biological status can be made.

In its fourth aspect, the present invention encompasses a method for treating a disease, status or condition in a mammalian patient, preferably a human, comprising the steps of:

i. administering to a patient in need of treatment a therapeutically effective amount of a pharmaceutical agent comprising the compound of Formula I and one or more pharmaceutically acceptable carriers, said compound having at least one Fab'-like moiety with specificity for the organ, tissue, cell, or tumor for which treatment is sought, whereby binding to the organ, tissue, cell, or tumor is effected, said compound also having at least one Fab'-like moiety with specificity for a therapeutic agent; and ii. administering to the patient in need of treatment a therapeutically effective amount of a therapeutic agent for which the compound of Formula I has specificity, whereby a treatment of the disease associated with the organ, tissue, cell, or tumor is effected.

In its fifth aspect, the present invention is directed to a method for diagnosing and treating a disease, medical condition or biological status comprising the steps of:

i. administering to a patient in need of diagnosis a diagnostically effective amount of a pharmaceutical agent comprising the trifunctional antibody-like compound of Formula I and one or more pharmaceutically acceptable carriers, the pharmaceutical agent having three specificities, the first specificity being for the organ, tissue or cells suspected of having a disease, condition, or status;

ii. administering to the patient a diagnostically effective amount of an imaging agent for which the compound of Formula I has a second specificity;

iii. making a diagnosis of the patient based upon the image obtained; and iv. administering to the patient a therapeutically effective amount of a therapeutic agent for which the compound of Formula I has a third specificity, should the diagnosis in Step iii so warrant.

In its sixth aspect, the present invention is directed to a method for treating a cell associated disease, medical condition or biological status in a mammalian patient, preferably human, comprising:

administering to a patient in need of treatment a therapeutically effective amount of a pharmaceutical agent comprising the compound of Formula I and one or more pharmaceutically acceptable carriers, said compound of Formula I having a first Fab'-like moiety thereon that is capable of binding to an antigen possessed by a target cell associated with said disease; said compound of Formula I further having a second and third Fab'-like moiety thereon with respective specificities for a receptor/receptor complex and an accessory molecule on the surface of a T-cell; said T-cell capable of destroying said target cell upon being activated, said T-cell becoming activated upon association of said receptor/receptor complex and said accessory molecule with said second and third Fab'-like moieties, when said compound of Formula I is bound to both said target cell and to said T-cell receptor/receptor complex and accessory molecule, said T-cell is activated and said target cell is in proximity to said activated T-cell, whereupon said T-cell is capable of destroying said target cell.

Alternatively, the methods for treating a disease, condition or biological status in a mammalian patient comprise administering to a patient in need of treatment, a therapeutically effective amount of the compound of Formula I to which has been bound one or more therapeutic agents for treating the diagnosed disease, condition or biological status.

DETAILED DESCRIPTION OF THE INVENTION

In its first aspect, the present invention is directed to a compound of Formula I, as previously described. Structurally, the compound of Formula I has a central moiety "L" which consists of from 1 to 2 linking or coupling agents that have covalently coupled with at least two members of the group consisting of $F_1ab'$, $F_2ab'$, and $F_3ab'$ to form a cross-link therebetween. The linking agents utilized in the present invention are bivalent and trivalent coupling agents, i.e., molecules that are capable of covalently binding to the free sulfhydryl (—SH) groups on at least 2 members of the group consisting of $F_1ab'$, $F_2ab'$ and $F_3ab'$. Preferred bivalent and trivalent coupling agents are the bis-malemides and tris-maleimides, respectively.

By the term "bis-maleimide" as used herein is meant an organic molecule having two maleimide moieties covalently bonded thereto wherein each maleimide moiety is positioned at or near substantially opposite ends of the molecule. Typical bis-maleimide molecules include N,N'-o-phenylenedimaleimide; N,N'-m-phenylenedimaleimide; N,N'-p-phenylenedimaleimide; N,N'-bis(maleimidopropionyl)-2-hydroxy-1,3-propanediamine ("BMP"); bis-(maleimido)methyl ether ("BMME") and the like. Preferred bis-maleimide molecules are BMP, which is commercially available from Sigma Chemical Co., St. Louis, Mo., and BMME which is commercially available from Boehringer Mannheim Corp., Indianapolis, Ind. In the present invention, two bis-maleimide compounds, which may be the same or different, react with the free sulfhydryl groups on three Fab'-like fragments to form the element "L" in the compound of Formula I.

By the term "tris-maleimide" as used herein is meant a compound of Formula II:

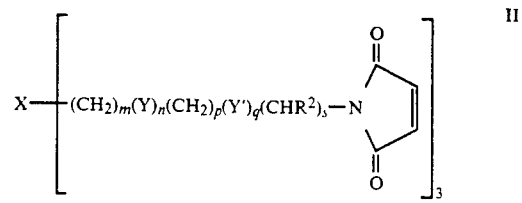

wherein X is

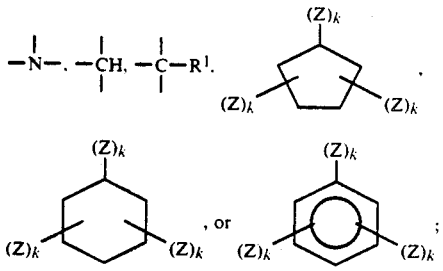

wherein k=1 or 0;
wherein q=1 or 0;
wherein Y' is

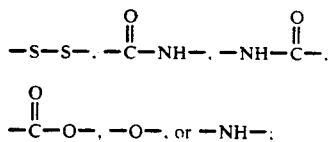

wherein Z is

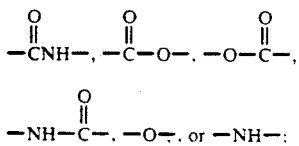

wherein s=1 or 0;
wherein n=1 or 0;
wherein Y is

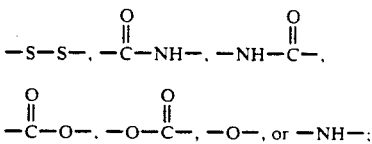

wherein p or m may be the same or different and are integers ranging from 0 to 20 with the provisos that when n=0, the sum of m and p is an integer ranging from 1 to 20, whereas when n=1, p and m are an integer that is at least 1 and the sum of p and m is an integer ranging from 2 to 20;

wherein $R^1$ is straight or branched chain lower alkyl having from 1 to 6 carbon atoms or lower alkocy having from 1–6 carbon atoms; and wherein $R^2$ is hydogen, phenyl, —COOH, or straight or branched chain lower alkyl having from 1–6 carbon atoms with the proviso that the lower alkyl moiety may be monosubstituted by —$NH_2$, —OH, or —COOH.

In the present invention, one or two tris-maleimides of Formula II may couple with the free sulfhydryl groups on the Fab'-like fragments to form the element "L". For example, one tris-maleimide compound may cross-link three Fab'-like fragments (e.g., $F_1ab'$, $F_2ab'$, and $F_3ab'$) to one another. Preferably, however, a single tris-maleimide is used to cross-link only two members of that group to one another, such that two tris-maleimides are required to cross-link all three Fab' fragments. The use of two tris-maleimides as the element "L" in the formation of a trifunctional antibody-like compound of the present invention is described in Scheme I herein.

Similarly, Scheme II herein describes the use of two bis-maleimides as generating the element "L."

It is also within the scope of the present invention to use a tris-maleimide compound in combination with a bis-maleimide to form a trifunctional antibody-like compound of the present invention.

The synthesis of the tris-maleimide compound represented by Formula II herein is described in detail in our co-pending U.S. pat. appl. Ser. No. 491,386 now U.S. Pat. No. 5,091,542, which was co-filed with the present application and is incorporated herein by reference. Typical trivalent coupling agents are tris-(2-N-maleimidoethyl)amine ("TMA") or tris[2-N-(maleoyl-glycyl)aminoethyl]amine ("TMG"), which are produced as described in Examples 1 and 2 herein, respectively.

In the present invention, both the bis- and tris-maleimides function as cross-linking agents when their maleimide moieties covalently couple to individual free sulfhydryl groups on at least two members of the group consisting of $F_1ab'$, $F_2ab'$, and $F_3ab'$. In the coupling reaction which is presented below, the maleimide moiety V is converted into the succinimido moiety VII upon coupling with a free sulfhydryl on an Fab'-like fragment VI.

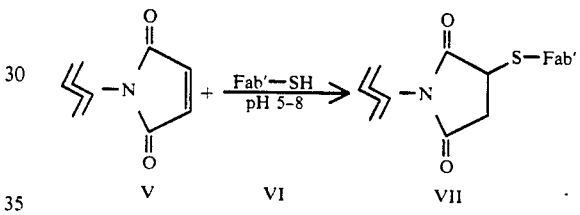

V VI VII

Hence, when cross-linking is complete, the bis-maleimide compounds form bis-succinimido moeities. Likewise, upon complete cross-linking, the tris-malemide compounds form tris-succinimido moieties. Accordingly, it is the bissuccinimido and tris-succinimido moieties, analogous to VII, which covalently cross-link $F_1ab'$, $F_2ab'$, and $F_3ab'$ and which constitute the element "L" in the present invention.

The elements $F_1ab'$, $F_2ab'$ and $F_3ab'$ of Formula I are individual Fab'-like fragments wherein two of the fragments may have the same antigenic specificity, but preferably, wherein each fragment has a unique antigenic specificity relative to the others. By the term "Fab'-like fragments" as used herein is meant to include Fab and/or Fab' fragments that have from 1-3 free sulfhydryl groups on their heavy chain, whether by natural occurrence, chemical modification or genetic engineering, and/or Fv fragments having from 1-3 sulfhydryl groups that have been genetically engineered onto either the heavy or light chain or onto a combination of both chains. The "Fv fragment," which is a fragment derived from either an antibody, an Fab' fragment, or an Fab fragment, contains the variable ("v") region of the antibody, Fab' fragment or Fab fragment, which region provides specificity for the antigen of interest.

In order for the genetically engineered Fab, Fab', and/or Fv fragments to be useful in the present invention, the 1-3 sulfhydryl groups, which are engineered into the fragments, must be positioned so as not to substantially interfere with the antigen binding capacity of the fragment. Those skilled in the art would known how to genetically insert one or more sulfhydryl containing amino acids into an Fab, Fab', or Fv fragment to produce an Fab'-like fragment suitable for use in the present invention. The determination of the number of the free sulfhydryl groups in proteins, such as Fab' fragments, is a technique that is well known in the art. U.S. Pat. No. 4,659,839, (Nicolotti, et al.), which issued on Apr. 21, 1987, describes such a method and is incorporated herein by reference.

Fab'-like fragments containing free sulfhydryl groups are produced by the enzymatic cleavage of a whole antibody at its hinge region. Typically, enzymatic cleavage of an antibody at or about the hinge region is effected by either pepsin or papain. By definition in the art, pepsin cleavage of a whole antibody, such as IgG$_1$, results in one F(ab')$_2$ fragment and one Fc' fragment. The subsequent reductive cleavage of the F(ab')$_2$ fragment that is obtained from the pepsin cleavage yields two Fab' fragments.

By definition in the art, papain cleavage of a whole antibody under reducing conditions results in two Fab fragments and one Fc fragment. An Fab fragment is structurally similar to an Fab' fragment in that both fragments contain the intact antigen binding regions of the antibody precursor. However, the Fab' fragment differs from the Fab fragment in that the Fab' fragment is slightly larger having more heavy chain. Typically, the Fab' fragment differs further from the Fab fragment by also having one or more additional sulfhydryl groups on its heavy chain.

Depending upon the species that is the source of the antibody, the number of disulfide bridges between the two heavy chains at the hinge region may vary. As a result, the number of free sulfhydryl (—SH) groups on the Fab and Fab' fragments may also vary from species to species. For example, the pepsin cleavage and subsequent reduction of mouse IgG$_1$, IgG$_{2a}$, and IgG$_{2b}$ antibody produces mouse Fab' fragments that have three free —SH groups. In contrast, the pepsin cleavage and subsequent reduction of human IgG$_1$ antibody produces Fab' fragments that have only two free —SH groups. Human IgG$_1$ is of interest because it has two free sulfhydryls (—SH) per Fab'.

The trifunctional antibody-like compound of the present invention can be synthesized by a number of routes. The route selected often depends upon the ultimate diversity of the three Fab'-like moieties thereon. For example, the trifunctional antibody-like compound may have three Fab'-like fragments only two of which are diverse, such as when F$_1$ab' and F$_2$ab' are directed to the same tissue, cell or tumor antigen and F$_3$ab' is directed to either a therapeutic or an imaging agent (e.g., Example 6 herein); or when F$_1$ab' is directed to a tissue, cell, or tumor antigen and F$_2$ab' and F$_3$ab' are both directed to the same imaging agent or to the same therapeutic agent.

The compound of the present invention may also have three Fab'-like fragments, each of which has its own unique specificity.

Regardless of the route of synthesis selected, the compound of the present invention is synthesized from any combination of three Fab'-like fragments, each independently having from 1-3 sulfhydryl groups and at least two of which Fab'-like fragments have different specificities, ultimately, these three Fab'-like fragments are reacted with either of two bivalent or two trivalent coupling agents, or with a combination thereof. However, the compound of the present invention, i.e., the compound of Formula I, is preferably made by a series of reactions between three Fab'-like fragments, each having two free sulfhydryl groups, and two trivalent coupling agents of Formula II. Such a reaction sequence is presented in Scheme I wherein F$_1$ab', F$_2$ab' and F$_3$ab' may be completely diverse or wherein any two of F$_1$ab', F$_2$ab', and F$_3$ab' may be the same.

In Scheme I, a first Fab'-like fragment, F$_1$ab', is reacted with an excess amount of a tris-maleimide compound XI in an aqueous buffer at pH 5-8, preferably pH 5-7. The tris-(or bis) maleimide compound, XI, may be dissolved in a small amount ($<10\%$ of aqueous reaction volume) of organic solvent to which is added the Fab'-like fragment to be derivatized. The amount and nature of the organic solvent required is dependent upon the hydrophobicity of the cross-linking agent X. The resultant product is a bi-covalently coupled F$_1$ab'-tris-maleimide complex XII that has a single reactive maleimide projecting therefrom. The reaction pH is important since at pH 5-8, preferably pH 5-7, the maleimide moieties on XI will couple only with free sulfhydryl (—SH) groups, whereas at pH $>$ 8, the maleimide moieties on XI can also couple to the amino groups of lysine residues on F$_1$ab'. The reaction pH is preferably controlled using citrate buffered saline (50 mM ammonium citrate, 100 mM NaCl, 1 mM diethylenetriaminepentaacetic acid ("DTPA"), pH 6.3) as the aqueous buffer.

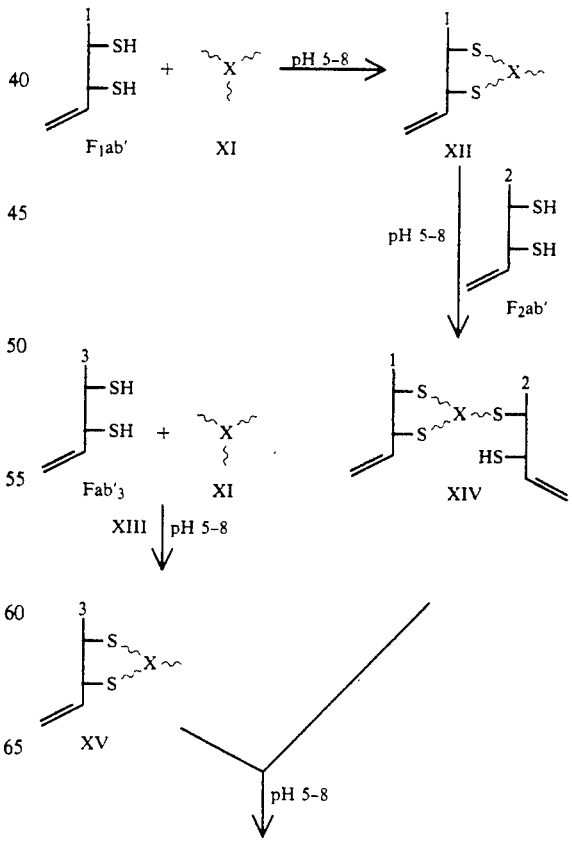

SCHEME I

-continued
SCHEME I

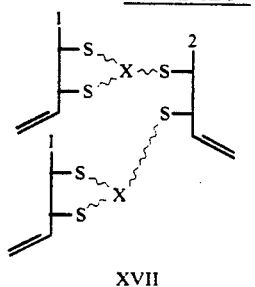

XVII

In the next sequence of reactions in Scheme I, the lone maleimide from XII is further coupled to a second Fab'-like fragment, $F_2ab'$, which has at least two free—SH groups. By utilizing an excess of $F_2ab'$ relative to XII, the formation of a bifunctional antibody-like compound XIV having two specificities predominates over the formation of a tri-antibody-like compound (not shown) having two $F_1ab'$ fragments. In some situations, however, it would be desirable to form a trifunctional antibody having two Fab' moieties that are the same, such as where both Fab' moieties are directed to the same antigen, the same imaging agent, or the same therapeutic agent.

In a third and separate reaction in Scheme I, a third Fab'-like fragment, $F_3ab'$, which may have the same or different specificity than $F_2ab'$, is covalently coupled to a tris-maleimide compound XI to produce the complex XV. The coupling is carried out in an aqueous buffer, pH 5-8, preferably pH 5-7. As previously described above, the aqueous buffer can also contain an appropriate water-miscible organic solvent (e.g., acetonitrile, DMF and the like) in an amount effective to dissolve the tris-maleimide XI. The tris-maleimide compound XI that is utilized in the third coupling may be the same or different than the tris-maleimide compound XI utilized in the first described coupling. The resultant product XV of this third coupling has a single reactive maleimide moiety projecting therefrom. Compound XV, with its single reactive maleimide, and XIV, which has a single free —SH, are combined in an aqueous buffer at pH 5-8, preferably pH 5-7. As previously disclosed, the tris-(or bis)maleimide compound may be dissolved in a small amount (<10% of aqueous reaction volume) of organic solvent to which is added the Fab'-like fragment to be derivatized is added. The combination of XV and XIV in the aqueous buffer at pH 5-8, preferably 5-7, causes the two compounds to covalently couple to produce the trifunctional antibody-like molecule XVII. The resultant product XVII is a compound according to Formula I, having utility as the active ingredient in the pharmaceutical agent of the present invention.

Fab'-like fragments as utilized in Scheme I are obtainable by the pepsin cleavage of human $IgG_1$ and the subsequent reduction of the $F(ab')_2$ fragment therefrom. In addition, Fab'-like fragments that have two free sulfhydryl groups at the hinge region are also obtainable from appropriate human-mouse chimeric antibodies. By appropriate human-mouse chimeric antibodies is meant antibodies that have a mouse variable region and a human constant region, such as from $IgG_1$. These antibodies yield Fab'-like fragments that have two sulfhydryl groups at the hinge region because the human constant region inherently includes the hinge region as a segment within it. Because the human constant region minimizes any chances of invoking an immune response when the chimeric antibody is injected into a human, these chimeric Fab'-like fragments with human constant regions are preferred for use as pharmaceutical agents over Fab'-like fragments from non-human sources.

Scheme II generically describes another preferred reaction sequence for making a compound according to Formula I. In Scheme II, a trifunctional antibody-like compound of the present invention is synthesized from two bismaleimide compounds and from 3 Fab'-like fragments, each fragment having three free —SH groups. Because the first Fab'-like fragment XIXa in Scheme II has three free —SH groups, it may oxidize or become oxidized to form XIXb, a fragment having both a disulfide (—S—S—) linkage and a single free —SH, the free —SH being suitable for coupling. However, as the first reaction in Scheme II indicates, coupling either the reduced $F_1ab'$, XIXa, or the oxidized $F_1ab'$, XIXb, with the bis-maleimide, XX, in an aqueous buffer pH 5-8, preferably pH 5-7, results in coupled products XXIa and XXIb respectively, which are functional equivalents. The bis-(or tris)maleimide compound may be dissolved in a small amount (<10% of aqueous reaction volume) of organic solvent, to which is added the Fab'-like fragment to be derivatized. Suitable water miscible organic solvents include DMF, acetonitrile and the like. In XXIa, two of the sulfhydryls are covalently coupled to opposite ends of a first bis-maleimide molecule. Similarly, in XXIb, two of the sulfhydryls are tied up due to formation of an intramolecular disulfide linkage (—S—S—). Functionwise, both XXIa and XXIb have one end of a bis-maleimide moiety coupled to a sulfhydryl such that the second end of the bis-maleimide with a reactive maleimide at its terminus extends therefrom.

SCHEME II

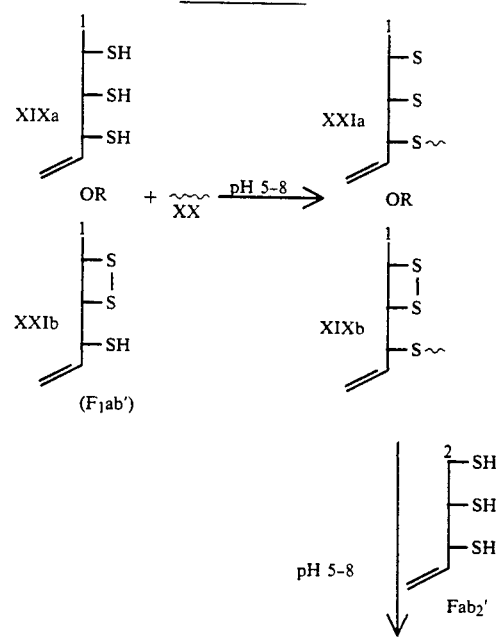

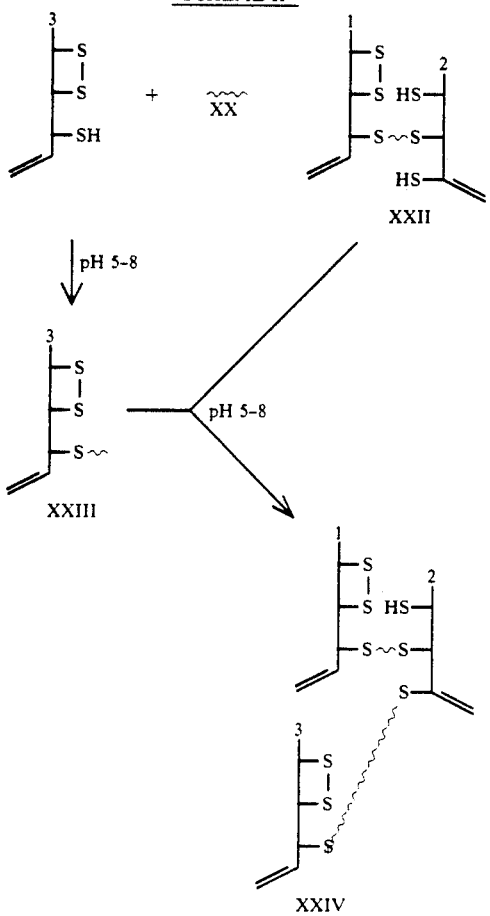

In an alternative embodiment (not shown) of the first reaction in Scheme II, XIXa could equally have been an Fab'-like fragment that had only a single sulfhydryl group which would have precluded the need for disulfide formation as in XIXb or bis-maleimide bridging as in XXIb.

For clarity, the next series of reactions in Scheme II show only the compound derived from XIXb, which has a bis-maleimide moiety acting as an intramolecular bridge between two of the three sulfhydryls in the molecule. In the next reaction, compound XXIb, which has a reactive maleimide moiety projecting therefrom, is combined in an aqueous buffer at pH 5-8, preferably pH 5-7, with a preferably less than equimolar amount of a second Fab'-like fragment, F$_2$ab', which has three free sulfhydryl groups. The resultant coupled product XXII is a bifunctional antibody-like compound that has two remaining free sulfhydryl groups, only one of which is needed for further coupling. In a separate reaction shown in Scheme II, a third Fab'-like fragment, F$_3$ab', is covalently coupled as in the first reaction in Scheme II, in an aqueous buffer at pH 5-8, preferably pH 5-7, to produce a covalently bound complex XXIII having a single maleimide projecting therefrom. Although F$_3$ab' is shown in Scheme II as being an Fab'-like fragment that has had two of its three free sulfhydryl groups bridged by a single bis-maleimide, two of the three sulfhydryls could also have been oxidized to form a disulfide. Alternatively, F$_3$ab' of Scheme II could equally have been an Fab'-like fragment with only a single free sulfhydryl group. In the final reaction of Scheme II, the complex XXIII, which has a reactive terminal maleimide moiety thereon, is coupled with the complex XXII, which has at least one free sulfhydryl group in an aqueous buffer pH 5-8, preferably pH 5-7. The resultant coupled product is a trifunctional antibody-like like compound XXIV that is encompassed by Formula I.

Accordingly, in Scheme II, trifunctional antibody-like compounds of the present invention can be produced when the first and third Fab'-like fragments initially have an odd number of free sulfhydryl groups, i.e., either 1 or 3.

Scheme III substantially parallels Scheme II, except that in Scheme III, the Fab'-like fragment that has been designated as F$_2$ab' has two free sulfhydrylgroups instead of three. As in Scheme II, all couplings between maleimide moieties and sulfhydryl groups are carried out in an aqueous buffer pH 5-8, preferably pH 5-7. As for Schemes I and II, the aqueous buffer used throughout Scheme III is preferably citrate buffered saline (50 mM ammonium citrate, 100 mM NaCl, 1 mM diethylenetriaminepentaacetic acid, pH 6.3). As for Schemes I and II, the bis-(or tris)maleimide compound may be dissolved in a small amount (<10% of aqueous reaction volume) of organic solvent to which is added the Fab'-like fragment to be derivatized. Thus, given the teachings of Schemes I-III, it should be apparent that Fab'-like fragments having a varied combination of free sulfhydryl groups could be combined to produce the trifunctional antibody-like compound of the present invention.

The trifunctional antibody-like compound of the present invention is particularly suited for use as a pharmaceutical agent having utility in diagnostics, therapeutics, and/or a combination thereof. By "diagnostics" as used herein is meant testing that is related to either the in vitro or the in vivo diagnosis of disease states or biological status (e.g. pregnancy, infertility, etc.) in mammals, preferably in humans. By "therapeutics" and "therapeutic/diagnostic combinations" as used herein is respectively meant the treatment or the diagnosis and treatment of disease states or biological status.

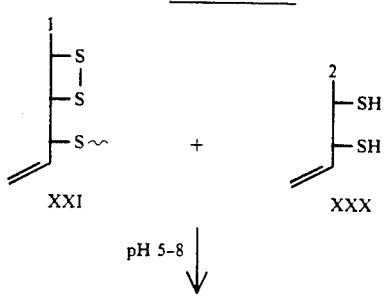

-continued
SCHEME III

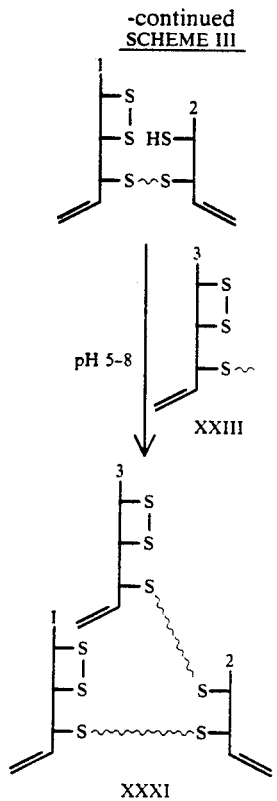

The tri-functional antibody-like compound has several embodiments which make it particularly useful as a pharmaceutical agent.

An embodiment of the pharmaceutical agent of the present invention is particularly suited for use as a combination diagnostic/therapeutic agent. In one embodiment that is suited for use as a combination diagnostic/therapeutic agent, the pharmaceutical agent of the present invention, which is also represented by Formula I, has three Fab'-like moieties with three different specificities.

The first Fab'-like moiety designated as $F_1ab'$, has specificity for an antigen, hapten or epitope (hereinafter collectively referred to as "antigen") on an organ, tissue or cell of interest and binds thereto. The second Fab'-like moiety, designated as $F_2ab'$ in Formula I, has specificity for a diagnostic imaging or dosimetric/isotope complex (e.g., a chelated nuclide or paramagnetic agent) that permits the imaging of the organ, tissue, or cell for which the first Fab'-like fragment has specificity; and/or the diagnosis of a condition, such as a cancer, associated with that organ, tissue or cell; and/or the calculation of a dosage of therapeutic agent to be administered based upon the image obtained. The third Fab'-like moiety, which is designated as $F_3ab'$ in Formula I, has specificity for a therapeutic agent that can optionally be administered to the patient should the expected condition present itself to a physician upon the imaging of the organ, tissue or cell via the immobilized $F_2ab'$ and its immobilized antigen. In this utility, the pharmaceutical agent of the present invention is bifunctional (i.e., both diagnostic and therapeutic) at the site of action.

Alternatively, in its utility as a pure diagnostic agent, the second and third Fab'-like moieties of the pharmaceutical agent of Formula I have specificity for the same or different diagnostic imaging or dosimetric complexes, either directly or indirectly. Similarly, in its utility as a pure therapeutic agent, both the second and third Fab'-like moieties of the pharmaceutical agent of the present invention have specificity for the same or different therapeutic agents, either directly or indirectly.

There are instances when a pharmaceutical agent of the present invention that has specificities for two different tumor antigens might be useful. For example, there is some evidence that melanoma may express either the p96.5 or the gp240 antigen or both. If this is true, then a compound of the present invention would be useful if it had $F_1ab'$ and $F_2ab'$ moieties with binding specificities directed toward these two antigens and $F_3ab'$ moiety with specificity directed toward either an imaging agent for diagnosis, or a chemotherapeutic or therapeutic isotope for treatment. A similar situation may exist in breast cancer, with some tumors expressing the $KS\frac{1}{4}$ antigen or CEA, or both. Hence a compound of the present invention having specificities for $KS\frac{1}{4}$ and CEA, via its $F_1ab'$ and $F_2ab'$ moieties, and for a diagnostic or therapeutic agent, via its $F_3ab'$ moiety, would likewise be useful. By analogy, similar applications of the pharmaceutical agent of the present invention to other dual antigen systems could be envisioned.

Regardless of the utility, the trifunctional antibody-like compound of the present invention has at least one Fab'-like fragment that has specificity for an antigen on an organ, tissue, cell, or molecule of interest (hereinafter "the first Fab'-like fragment"). By "tissue" as used herein is meant both normal tissues and abnormal tissues. By way of example, "abnormal tissues" include tumors, cancers precancers, neoplasms, necrotic tissue and the like.

A number of tumor associated antigens are well known to those skilled in the art. By way of example and not limitation, these tumor antigens include alpha-fetoprotein, c-erbB-2, cancer antigen 15-3 ("CA 15-3"), CA 19-9, CA 125, CA 195, CA 549, carcinoembryonic antigen ("CEA"), cathepsin D ("cath D"), cytokeratins, DU-PAN-2, Epidermal Growth Factor Receptor ("EGF-R"), estrogen receptor, c-myc, N-myc, prostate specific antigen (PSA), ras, tumor associated antigen-72 ("TAG-72"), tumor associated antigen-4 ("TA-4"), $KS\frac{1}{4}$ and the like. Monoclonal antibodies to many of these tumor antigens and others have already been produced. Publications disclosing the production of these and other monoclonal antibodies are tabulated in U.S. Pat. No. 4,814,438 (Armour et al.) which issued on Mar. 21, 1989 and is incorporated herein by reference.

Preferably, the imaging agent, for which $F_2ab'$ and/or $F_3ab'$ may have specificity, permits the extra corporeal imaging of an in vivo organ or tissue for the diagnosis of any disease associated therewith. Typically, the imaging agent is a physiologically compatible chelate complex that has been formed between either a chelating agent and a radionuclide or a chelating agent and a paramagnetic metal ion. Radionuclides permit the imaging of tissue and/or organs by gamma scintillation photometry whereas paramagnetic metal ions permit the visualization of organs and/or tissues by magnetic resonance imaging (MRI). Both imaging techniques are well known to those skilled in the in vivo imaging arts. By "physiologically compatible chelate complex" as used herein is meant a complex between a chelating agent and a paramagnetic metal ion or radionuclide that does not permit physiologically incompatible amounts of paramagnetic metal ion or radionuclide to dissociate from the complex in vivo. Low dissociation constants for the physiologically compatible chelate complexes insure that there is little, if any, release of toxic heavy metal ions or radionuclides which may be absorbed with deleterious effects in various tissues of the mammalian body. Preferably, the dissociation constant of the physiologically compatible chelate complex is $10^{-16}$ or lower; more preferably, $10^{-18}$ or lower; most preferably, $10^{-20}$ or lower.

Suitable chelating agents for the radionuclides and/or paramagnetic metal ions are polyacidic organic molecules that further contain organic nitrogen, phosphorous, oxygen or sulfur. By way of example, suitable chelating agents include ethylenediaminetetraacetic acid ("EDTA"), ethanolaminethioureabenzyl-EDTA ("EOTUBE"), diethylenetriaminepentaacetic acid ("DTPA"), methylthioureabenzyl DTPA ("MeTUBD"), 1,4,7,10-tetrazacyclododecane-N',N'',N''',N''''-tetraacetic acid ("DOTA"), L-aminobenzyl-EDTA, 1,5,9,13-tetraazacyclohexadecane-N,N', N'', N'''-tetraacetic acid ("HETA"), 1,4,7,10-tetraazacyclotridecane'N, N',N'', N'''-tetraacetic acid ("TRITA"), 1,4,8,11-tetraazacyclotetradecane-N,N', N'', N'''-tetraacetic acid ("TETA"), and the like. Methods for preparing bifunctional derivatives of EDTA, DTPA and their analogs are described in Meares et. al., U.S. Pat. No. 4,622,420, issued Nov. 11, 1986, which is herein incorporated by reference. The methods for preparing bifunctional derivatives of DOTA, TRITA, HETA, and TETA are described in detail in Meares et. al., U.S. Pat. No. 4,678,667 issued Jul. 7, 1987 herein incorporated by reference, and in Moi et. al., *J. Am. Chem. Soc.* 110: 6266 (1988). The mentioned chelating agents all form physiologically compatible chelate complexes with a variety of metal ions. Other suitable organic chelating agents are disclosed in U.S. Pat. No. 4,647,447 (Gries et al.) which is incorporated herein by reference.

Radionuclides that are suitable for imaging organs and tissues in vivo via diagnostic gamma scintillation photometry include the following: gamma emitting radionuclides: $^{111}$In, $^{113m}$In, $^{67}$Ga, $^{68}$Ga, $^{99m}$Tc, $^{51}$Cr, $^{197}$Hg, $^{203}$Hg, $^{169}$Yb, $^{85}$Sr and $^{87}$Sr. These $\gamma$ emitting radionuclides are chelatable when in ionic form. Of these radionuclides, $^{111}$In (III) is preferred. The preparation of chelated radionuclides that are suitable for binding by Fab' fragments is taught in U.S. Pat. No. 4,659,839 (Nicoletti et al.) which is incorporated herein by reference.

Paramagnetic metal ions that are suitable for use as imaging agents in MRI include the lanthanide elements of atomic number 57-70, or the transition metals of atomic numbers 21-29, 42 or 44. U.S. Pat. No. 4,647,447 (Gries et al.) teaches MRI imaging via chelated paramagnetic metal ions and is incorporated herein by reference.

The third Fab'-like fragment that is a component of the trifunctional antibody like compound of the present invention has specificity for a therapeutic agent. By "therapeutic agent" as used herein is broadly meant any agent administered under order of a physician to treat a disease, condition, or biological status that has manifested itself.

As alternative embodiments, the second and/or third Fab'-like fragments are capable of independently having specificity for one or more therapeutic agents either directly or indirectly. Specificity for a therapeutic agent is "direct" when the Fab' fragment is specific for the therapeutic agent itself. Examples of therapeutic agents "directly" bound by the second and/or third Fab'-like fragment are the chelate complexes that are formed between chelating agents and radionuclides that are $\beta^-$-emitters. By "$\beta^-$-emitters" as used herein is meant a chelatable radionuclide that emits $\beta^-$ particles of sufficient energy and frequency so as to provide a beneficial effect in the treatment of a disease, condition or biological status. Suitable $\beta^-$-emitters include $^{67}$Cu, $^{186}$Rh, $^{188}$Rh, $^{189}$Rh, $^{153}$Sm, $^{90}$Y, and $^{111}$In (Aüger). The $\beta^-$-emitters are chelatable when in ionic form, typically when in the +1 to +4 oxidation state. Selection of a $\beta^-$-emitter depends upon a number of factors such as the type of disease, condition and age of the patient, extent of the disease, prognosis based upon treatment, site of localization and the like. An especially preferred $\beta^-$-emitter is $^{90}$Y (III).

Suitable chelating agents for the $\beta^-$-emitters in their ionic form are the polyacidic organic molecules that contain organic nitrogen, phosphorus, oxygen or sulfur. By way of example, suitable chelating agents include ethylenediaminetetraacetic acid ("EDTA"), ethanolaminethioureabenzyl-EDTA ("EOTUBE"), diethylenetriaminepentaacetic acid ("DTPA"), methylthioureabenzyl DTPA ("MeTUBD"), 1,4,7,10-tetrazacyclododecane-N',N'',N''',N''''-tetraacetic acid ("DOTA"), L-aminobenzyl-EDTA, 1,5,9,13-tetraazacyclohexadecane-N,N',N'',N'''-tetraacetic acid ("HETA"), 1,4,7,10-tetraazacyclotridecane-N,N',N'',N'''-tetraacetic acid ("TRITA"), 1,4,8,11-tetraazacyclotetradecane-N,N',N'',N'''-tetraacetic acid ("TETA"), and the like. The synthesis of these compounds has already been referenced herein. Other suitable organic chelating agents are disclosed in U.S. Pat. No. 4,647,447 (Gries et al.) which issued on Mar. 3, 1987 and is incorporated herein by reference.

Particularly preferred therapeutic agents that are capable of direct binding to an Fab'-like moiety or a compound of the present invention are $^{90}$Y-MeTUBD, $^{90}$Y-DTPA, $^{90}$Y-DOTA and dumbbell shaped derivatives thereof.

The trifunctional antibody-like compounds of the present invention may also be used with pharmaceutically acceptable chelate complexes that are formed from a novel class of bifunctional "dumbbell shaped" chelating agents. These dumbbell shaped chelating agents have EDTA or a derivative thereof at a first end of a linker arm and the same or a different chelating agent at the second (opposite) end of the linker arm. Preferred chelating agents for use at the opposite and of said linker arm are EQTUBE, DPTA, MeTUBD, DOTA, L-aminobenzyl-EDTA, HETA, TRITA and TETA.

The dumbbell shaped chelating agent can be used as a simple method for varying the diagnostic or therapeutic metal ion at the target site without the need to change the antibody specificity. For example, assume that a trifunctional antibody-like compound of the present invention is immobilized, via $F_1ab'$, at a target site, and that $F_2ab'$ has specificity for the In-EDTA complex. The $F_2ab'$ moiety is thus capable of binding the imaging agent, $^{111}$In-EDTA, or a ground state (or non-radioactive) In-EDTA complex. Upon administering a dumbbell shaped chelating agent having an In-EDTA complex at its first end, the In-EDTA end becomes bound by $F_2ab'$. By varying the chelating agent at the second end of the dumbbell, the specificity of the chelating agent for different imaging agents (e.g., radioactive or paramagnetic metal ions) or different therapeutic metal ions (e.g., β⁻emitters) is also varied. The making and use of these dumbbell shaped chelating agents is fully described in commonly assigned U.S. Pat. No. 5,005,289, which is incorporated herein by reference. Thus, the use of only a single trifunctional antibody-like compound of the present invention in conjunction with the dumbbell shaped chelating agents enables one skilled in the art to produce a whole family of imaging and/or therapeutic agents.

The dumbbell shaped chelating agents are also useful for binding two radioactive $^{90}$Y(III) ions to a single Fab'-like moiety, effectively doubling the localized dose without the need to double the amount of trifunctional antibody-like compound bound to the target site.

In contrast to having direct specificity for a therapeutic agent as discussed above, the compound of the present invention may also have indirect specificity for a therapeutic agent. The specificity of the compound of the present invention for a therapeutic agent is "indirect" when at least one of the Fab'-like moieties thereon have specificity for an enzyme. By "enzyme" as used herein is meant a naturally occurring or genetically engineered enzyme or active fragment thereof.

In some circumstances, it may be desirable to administer the compound of Formula I with the enzyme already bound by the Fab'-like moiety. In this embodiment, the compound of the present invention binds at the site of action, e.g., a tumor, via at least one of its Fab'-like moieties. The enzyme, which has become immobilized at the site of action, via one of the Fab'-like moieties, is capable of converting its substrate to product, preferably, via cleavage. When the administered substrate is bound to a therapeutic agent, the enzyme cleaves its substrate to cause a localized release of the therapeutic agent at the site of action, e.g., the tumor.

Preferably, the therapeutic agent has little or no biological activity until cleaved from the substrate. Using this embodiment, one skilled in the art can easily vary the number and type of therapeutic agents bound to any particular enzyme substrate. The resulting variation permits the treating physician to tailor both the dosage and the treatment to the individual patient's needs, depending upon such factors as the condition presented, the severity of the condition, the patient's sensitivity to particular pharmaceuticals, and the condition's response to previously administered pharmaceuticals. A treating physician could even co-administer two or more therapeutic agents bound to the same, or to a similar substrate, or co-bound to the same enzyme substrate to provide a localized synergistic effect at the organ, tissue or tumor of interest. Because the therapeutic agent is only released by enzymatic activity at the site of action, the therapeutic effect is maximal at the site of action. As a result, adverse effects caused by the released therapeutic agent are generally minimized in other (healthy) parts of the body particularly with increasing distance from the site of action. The ability to minimize generalized adverse effects is particularly important with therapeutic agents that cannot discriminate between healthy and diseased tissue, organs, or cells, such as the cytotoxic agents.

In this latter embodiment, the enzyme substrate is preferably conjugated to a cytotoxic agent to produce the therapeutic agent of Formula III:

Substrate-Cytotoxic Agent     III wherein
the Substrate is the substrate for an enzyme or active fragment thereof, wherein reaction of the enzyme with the Substrate-Cytotoxic Agent causes the release of the Cytotoxic Agent from the Substrate; and the Substrate and the Cytotoxic Agent are bonded together through an ether, thioether, ester, amide, amino, hydrazido, carbonate, carbamate, thiocarbamate, thioester, thioamide, or thiocarbonate group formed from the appropriate reactive group on the Substrate and a hydroxy, thioether, amine, amido, hydrazido, carboxy, or carbamato group on the Cytotoxic Agent. Alternatively, the Substrate may be a precursor for a Cytotoxic Agent. See, for example, Chen et al., U.S. application Ser. No. 07/305,900, filed Feb. 2, 1989, herein incorporated by reference which was abandoned in favor of continuation-in-part application Ser. No. 07/468,441, filed Jan. 22, 1990, and the two continuation applications Ser. Nos. 07/872,468 and 07/909,924, which were filed on Apr. 23, 1992 and Jul. 6, 1992 respectively, all three now pending.

In its broadest aspect, the Substrate component of Formula III is any enzyme substrate that can be cleaved in vivo by an enzyme that is physiologically compatible in the patient to whom the therapeutic agent of Formula III has been administered. Preferably, the enzyme should not naturally circulate in the patient, since a circulating enzyme could cleave Formula III releasing the cytotoxic agent before it could be localized via capture by the compound of Formula I. Preferred Substrates for the enzyme component of Formula III are substrates for non-mammalian enzymes such as beta-lactamase, L-pyroglutamate aminopeptidase, beta-galactosidase, or D-amino acid peptidase. A particularly preferred substrate is a compound which has a beta-lactam moiety such as a penicillin, a penem, a carbapenem, cephalosporin, 1-carbadethiacephalosporin, or 1-oxadethiacephalosporin. The correspondingly particularly preferred enzyme is a beta-lactamase, most preferably a beta-lactamase taken from *Enterobacter cloacae*.

By the term "Cytotoxic Agent" as used herein means compounds that are useful in the treatment of neoplasms, whether benign or malignant. Such drugs include, in general, alkylating agents, antiproliferative agents, tubulinbinding agents, cytotoxins in general, and the like. Preferred classes of such compounds are the nitrogen mustard agents, the vinca alkaloids, the daunomycin family, the mitomycins, the bleomycins, the cytotoxic nucleosides, the pteridine family of drugs, the podophyophyllotoxins, the sulfonylureas (as described in European Patent Publication No. 222,475, published May 20, 1987), and low-molecular-weight toxins such as the trichothecanes and the colchicines. Particularly preferred members of those classes include, for example, doxorubicin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, etoposide, melphalan, vinblastine, vincristine, leurosidine, vindesine, leurosine, trichothecene, desacetylcolchicine, and the like. In order to facilitate conjugation between the Substrate and the Cytotoxic Agent, unimportant chemical modifications may be made by the ordinarily skilled chemist to the preferred and generally described compounds. Preferred Substrate-Cytotoxic Agent compounds of Formula III are prepared from the preferred Cytotoxic Agents and enzyme Substrates noted above.

In yet another embodiment, the compound of the present invention is capable of directing, activating, or otherwise sensitizing a T-cell against a target cell that is intended to be killed. In this embodiment, which is expressed in terms of the elements of Formula I, L is one or two moieties for cross-linking $F_1ab'$, $F_2ab'$ and $F_3ab'$;

$F_1ab'$ is an Fab'-like fragment of a polyclonal or monoclonal antibody having specificity of an antigen expressed by the cell or tumor of interest; and $F_2ab'$ and $F_3ab'$ have specificity for the T-cell receptor/receptor complex and accessory molecule respectively on the surface of the T-cell.

The accessory molecule may be CD2, CD4, CD5 or other T-cell surface markers. In this embodiment, the compound of the present invention, which is affixed to the T-cell, via $F_2ab'$ and $F_3ab'$, is capable of binding to antigen expressed by the target cell or tumor (cell) via $F_1ab'$ which is at the end of a linker arm encompassed by L.

The production of monoclonal antibodies to T-cell receptors C/receptor Complex and accessory molecules is within the ordinary skill of those working in the art, the production of monoclonal antibodies to a variety of cellular and tumor antigens is already described in the art.

Given the teaching of the present invention, a whole family of T-cell activating compounds, having specificity for a variety of cell and/or tumor expressed antigens can be made by those skilled in the art. Once $F_2ab'$ and $F_3ab'$ are made, one need only vary $F_1ab'$. Coupling is accomplished as described herein using two bivalent or two trivalent coupling agents, or a combination thereof.

The second aspect of the present invention is directed to the use of the trifunctional antibody-like compound of Formula I as the active ingredient in a pharmaceutical composition. More particularly, the second aspect of the present invention is directed to a pharmaceutical composition comprising:

(a) the compound of Formula I as described herein; and (b) one or more pharmaceutically acceptable carriers.

The pharmaceutical composition of the present invention may be administered by parenteral injection, i.e., intravascularly, intraperitoneally, subcutaneously, intramuscularly, or topically using forms and methods known to the pharmaceutical art. In general, the preferred form of administration is intravascularly. For the parenterally administered pharmaceutical composition and method of the present invention, the active ingredients of Formula I typically be administered in admixture with suitable pharmaceutical diluents, excipients, or carriers (collectively referred to herein as "carriers") suitably selected with respect to the intended form of administration and consistent with conventional pharmaceutical practices.

For topical administration, such as for melanomas, therapeutically effective amounts of one or more compounds of the present invention can be combined with pharmaceutically acceptable creams, oils, waxes, gels or the like. Regardless of the route of administration selected, the compound of the present invention is formulated into a pharmaceutically acceptable dosage form by conventional methods known to those skilled in the art. The compound of Formula I may also be formulated into a pharmaceutical agent of the present invention using one or more of its pharmacologically acceptable base addition salts. Moreover, the compound of Formula I or its salts may be used in a suitable hydrated or lyophilized form. Preferably, the compound of the present invention is administered in unit dosage form.

In its further aspects, the present invention is directed to methods for diagnosing, for treating and for both diagnosing and treating a disease utilizing the pharmaceutical agent of the present invention. Thus, in its third aspect, the present invention is directed to a method for diagnosing a disease, medical condition or biological status in a mammalian patient, preferably a human, comprising:

i. administering to the patient in need of diagnosis a diagnostically effective amount of a pharmaceutical agent comprising the compound of Formula I and one or more pharmaceutically acceptable carriers, said compound having at least one Fab'-like moiety with specificity for the organ, tissue, cell, or tumor about which a diagnosis is sought, said compound also having at least one Fab'-like moiety with specificity for an imaging agent; and ii. administering to the patient in need of diagnosis a diagnostically effective amount of an imaging agent capable of being bound by said compound of Formula I, whereby the diagnosis of a disease, medical condition or biological status can be made.

In the method for diagnosing, which is described above, the compound of Formula I, via one or two of its Fab'-like moieties, may have specificity for one or two antigens that are expressed by the tissue, organ, cell or tumor or interest. These antigens may be the same or different as previously discussed herein. Alternatively, two Fab'-like moieties on the compound of Formula I may be the same or different but have specificity for the same antigen expressed by the tissue, organ, cell or tumor of interest. The two Fab'-like moieties are the same and have the same specificity when they are derived from the same monoclonal antibody. The two Fab'-like fragments are different but have the same specificity when they are derived from a polyclonal antibody to the same antigen or preferably, from different monoclonal antibodies to the same antigen. Examples of the latter monoclonal antibodies are CEM and ZCE of Example 3, both of which have specificity for carcinoembryonic antigen (CEA).

In various embodiments of the above described method, the compound of Formula I may have specificity for one or two imaging agents which may be the same or different. The various types of medical imaging agents have already been discussed herein. Those skilled in the art are familiar with their use.

In its fourth aspect, the present invention also encompasses a method for treating a disease, status or condition in a mammalian patient, preferably a human, comprising the steps of:

i. administering to a patient in need of treatment a therapeutically effective amount of a pharmaceutical agent comprising the compound of Formula I and one or more pharmaceutically acceptable carriers, said compound having at least one Fab'-like moiety with specificity for the organ, tissue, cell, or tumor for which treatment is sought whereby binding to the organ, tissue, cell or tumor is effected, said compound also having at least one Fab-like moiety with specificity for a therapeutic agent; and ii. administering to the patient in need of treatment a therapeutically effective amount of a therapeutic agent for which the compound of Formula I has specificity, whereby a treatment of the disease associated with the organ, tissue, cell, or tumor is effected.

In the method for treating a disease, the compound of Formula I may have specificity, for one or two antigens expressed by the organ, tissue, cell or tumor for which a treatment is desired. The two antigens may be the same or different. Moreover, as discussed in the method for diagnosing, two Fab'-like moieties derived from different antibodies having specificity for the same antigen (but possibly different epitopes) may also be used.

In various embodiments of the method for treating a disease, the compound of Formula I may have specificity for one or two therapeutic agents, directly or indirectly as described herein. When at least one of the Fab'-like fragments has specificity for a therapeutic agent indirectly, such as when it has specificity for an enzyme capable of releasing a therapeutic agent from a substrate-therapeutic agent complex, more than one dose of the substrate-therapeutic agent complex can be administered and acted upon by the enzyme without the need to repeat Step (i), i.e., without the need to readminister a compound of Formula I. It is also within the scope of the method for treatment to vary the therapeutic agent bound to the substrate to provide a multi-therapeutic agent treatment. The varied substrate-therapeutic agent complexes can be administered together or sequentially, depending upon such factors as age and condition of the patient; type of disease, status, or condition; response to previous treatment, possibility of drug-drug interaction, and treating physician.

A method for both diagnosing and treating a disease in a mammalian patient is also within the scope of the present invention. The method comprises the steps of
  i. administering to a patient in need of diagnosis, a diagnostically effective amount of a pharmaceutical agent comprising the compound of Formula I and one or more pharmaceutically acceptable carriers, said compound of Formula I having one Fab'-like moiety with specificity for the organ, tissue, cell, or tumor about which diagnosis is sought, a second Fab'-like moiety with specificity for an imaging agent, and a third Fab'-like moiety with specificity for a therapeutic agent;
  ii. administering to the patient a diagnostically effective amount of an imaging agent for which the compound of Formula I has a specificity;
  iii. making a diagnosis of the patient based upon the image obtained; and
  iv. administering to the patient a therapeutically effective amount of a therapeutic agent for which the compound of Formula I has specificity, should the diagnosis in Step iii so warrant.

As an addition or alternative to Step (iii) above, the treating or diagnosing physician can use the image obtained to calculate the dose of therapeutic agent, if any, to be administered to the patient. The image provides the physician with information as to uptake of the compound of Formula I, extent and location of disease and the like.

The present invention also encompasses a method for treating a cell associated disease in a mammalian patient comprising:
  administering to a patient in need of treatment a therapeutically effective amount of a pharmaceutical agent comprising the compound of Formula I and one or more pharmaceutically acceptable carriers, said compound of Formula I having a first Fab'-like moiety thereon that is capable of binding to an antigen possessed by a target cell associated with said disease; said compound of Formula I further having a second and third Fab'-like moiety thereon with respective specificities for a T-cell receptor/receptor complex and an accessory molecule on the surface of a T-cell; said T-cell capable of destroying said target cell upon being activated, said T-cell becoming activated upon association of both said T-cell receptor/receptor complex and said accessory molecule with said second and third Fab'-like moieties respectively, said activated T-cell and said target cell being in proximity when said compound of Formula I is bound to said target cell, said T-cell receptor/receptor complex, and said accessory molecule, whereupon said activated T-cell is capable of destroying said target cell.

The above method may be used to activate a patient's own T-cells, in vivo or in vitro. Alternatively, the compound of the present invention can be administered with exogeneous T-cells, either separately, or via coadministration in a common pharmaceutical carrier. Those skilled in the art know how to collect, select, culture and administer T-cells.

The nucleic acid sequences, and thus the amino acid sequences, for the alpha and gamma subunits of T-cell antigen receptors are disclosed in U.S. Pat. Nos. 4,873,190 and 4,874,845 respectively and are incorporated herein by reference. Given the teaching of the present invention, one skilled in the art could prepare Fab' like fragments having specificity for either of these T-cell receptor complex proteins.

Regardless of the route of administration selected in any of the above methods, a non-toxic but diagnostically and/or therapeutically effective quantity of one or more compounds of this invention is employed in any respective diagnosis and/or treatment. The dosage regimen for diagnosing and treating diseases, conditions, or status with the compound of this invention is selected in accordance with a variety of factors, including the type, age, weight, sex, and medical condition of the patient, the severity of the condition, the route of administration, and the ultimate compound employed in the treatment. A physician or veterinarian of ordinary skill can readily determine and prescribe the effective amount of the pharmaceutical agent required to diagnose a disease or arrest the progress of a condition. In so proceeding, the physician or veterinarian could employ relatively low doses at first and subsequently increase the dose until a maximum response is obtained. Because the trifunctional antibody-like compound of the present invention localizes the therapeutic agent, much lower doses of therapeutic agent would be effective than by conventional administration.

In practicing the latter described method, which encompasses both the methods for diagnosing and treating, a physician or veterinarian or someone under their direction would administer a diagnostically effective amount of the compound of the present invention to a patient in need of diagnosis. The compound would be selected so that it contained an Fab'-like fragment that had specificity (i.e., it would bind) to an antigen on the organ, tissue or cell of interest. After an incubation period in which the pharmaceutical agent of the present invention was allowed to bind, the physician would administer an imaging agent for which the pharmaceutical agent of the present invention has a second specificity. Based upon the image obtained, a diagnosis of the patient's disease, condition or status would be made. In those patients for which treatment is warranted, the physician, veterinarian or someone under his control would administer a therapeutically effective amount of a therapeutic agent suited for treatment of the disease, condition or status. If no disease, condition or status warranting treatment is presented, no therapeutic agent need be administered.

By the term "therapeutically effective amount" as used herein is generally meant an amount of the therapeutic agent sufficient to cause the desired response in all or a portion of the target organ, tissue or cells to which the trifunctional antibody-like compound has bound. By the term "therapeutically effective amount" as specifically relates to either the Substrate-Cytotoxic Agent of Formula III or the chelate complex of a $\beta$-emitting radionuclide is meant an amount sufficient to cause some target neoplastic cell death, or an amount sufficient to keep a neoplastic disease in remission, or, in general, in an amount sufficient for prophylaxis.

A particularly unique feature of the present invention is that the physician or veterinarian can see, via the imaging agent, exactly where the therapeutic agent will be localized by the immobilized compound of Formula I. This is because the immobilized compound of Formula I, which binds to the imaging agent, will also bind to the therapeutic agent. This feature allows the treating physician to vary the treatment (e.g., the therapeutic agent) or elect no treatment depending upon the extent of the disease or its invasion of particularly sensitive organs.

By way of example, the latter method could be used in the diagnosis and treatment of adenocarcinoma of the colon. In particular, the first Fab'-like fragment (or moiety) in the compound of Formula I would have specificity for carcinoembryonic antigen ("CEA"); the second Fab'-like fragment would have specificity for an imaging agent, e.g., a chelated $^{111}$In (III) complex, such as $^{111}$In-EDTA or $^{111}$In-EOTUBE, and the third Fab'-like fragment would have specificity for a therapeutic agent, e.g., a chelated $^{90}$Y (III) complex, such as $^{90}$Y-DTPA or $^{90}$Y-MeTUBD.

The following examples are given for illustration only and should not be construed as limiting the invention in spirit or scope.

DESCRIPTION OF THE PREFERRED EMBODIMENT

Example 1

Tris-(2-N-maleimidoethyl)amine ("TMA")

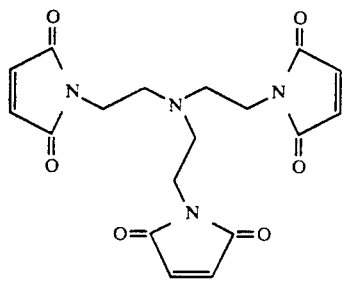

To 15 g of NaHCO$_3$ in a 250 ml Erlenmeyer flask was added 100 ml of cold water and the mixture was stirred in an ice bath until the reaction mixture was at 0° C. To 80 ml of the supernatant solution in a 1000 ml round bottom flask was added 1.8 ml of tris(2-aminoethyl)amine and the mixture was cooled 0° C. in an ice bath. To the cooled reaction mixture was added with stirring 6.2 g of finely ground N-methoxycarbonylmaleimide and the mixture was stirred for an additional 10 minutes in the ice bath. Thereafter, 240 ml of water was added to the mixture and it was stirred at room temperature for 30 minutes. Then, the pH of the solution was adjusted to between pH 6-7 with concentrated HCl and the volume was reduced to 100 ml by evaporation under reduced pressure. The pH of the resulting solution was adjusted to 10 with saturated Na$_2$CO$_3$ solution. The resultant solution was extracted 3× with 200 ml of ethyl acetate and the combined organic phases were washed 2× with 100 ml of H$_2$O. The organic phase was dried (30 g Na$_2$SO$_4$), filtered, and evaporated under reduced pressure to dryness. The residue was dissolved in 40 ml of warm ethyl acetate, filtered (Buchner funnel), and evaporated under reduced pressure to dryness. The residue was dissolved at a ratio of 5 ml/g (residue) using ethyl acetate:methylene chloride (1:3/v:v). To a 150 ml Lobar silica gel column that had been pre-equilibrated with 2 bed volumes of ethyl acetate:methylene chloride (1:3/v:v) was added a 5 ml aliquot of the dissolved residue. The column was eluted with the same solvent at 4 ml/min and the TMA fraction, as monitored at A$_{280}$, was collected in a 500 ml round bottom flask. The TMA fraction was evaporated to dryness. Additional 5 ml aliquots of the dissolved residue were similarly treated and the corresponding TMA fractions were evaporated by dryness. The TMA residues were dissolved in 10 ml of the elution solvent, pooled together and evaporated under reduced pressure to dryness. The combined residue was dissolved in 40 ml of ethyl acetate:isopropyl ether (3:1/v:v) using a 60° C. water bath, filtered, and cooled sufficiently until the TMA precipitated out as crystalline yellow needles. The resultant TMA crystals were collected on a sintered glass funnel, washed 2× with 5 ml of isopropyl ether, and dried overnight under vacuum, M.P. 132°-133° C.

| Analysis for C$_{18}$H$_{18}$N$_4$O$_6$ (MW = 386.36). | | | |
|---|---|---|---|
| Calcd: | C, 55.95; | H, 4.70; | N, 14.50. |
| Found: | C, 55.54; | H, 4.69; | N, 14.45. |

$^1$H NMR $\delta_{TMS}$ $^{CDCl_3}$ (300 MHz): 6.65(6H,s); 3.49(6H,t); and 2.68(6H,t).

I.R. (KBr): 1700 cm$^{-1}$ (C=O).

U.V. (DMF): peak at 272, molar extinction coefficient = 1920.

Example 2

Tris[2-N-(maleoylglycyl)aminoethyl]amine ("TMG")

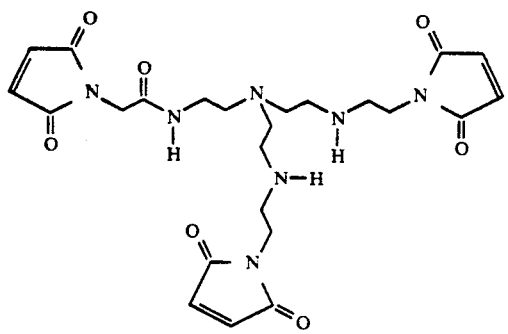

Glycine (1.5 g, 20 mmol) in saturated NaHCO$_3$ (100 ml) was vigorously stirred at 0° C. with finely ground N-methoxycarbonylmaleimide (3.1 g, 20 mmol). After 10 minutes, the solution was diluted with 400 ml of water and stirred at room temperature for 40 min. The pH was adjusted to −7 with concentrated HCl and evaporated in vacuo to about 50 ml. The solution was acidified to pH −2 with 3N HCl and extracted two times with 100 ml of ethyl acetate. The combined ethyl acetate extract was washed with water, dried over anhydrous Na$_2$SO$_4$, and evaporated to dryness. The crude product was divided into three portions and purified on a 150 ml Lobar reverse phase C$_{18}$ column eluted with 30% MeOH/H$_2$O: yield 1.85 g, 60% of maleimidoacetic acid, m.p. 110° C.

$^1$H NMR (D$_2$O): δ4.30(2H, s), and 6.95(2H, s).

IR (KBr) 1710 cm$^{-1}$ (C=O)

Maleimidoacetic acid (155 mg, 1.0 mmol) in 5 ml of diglyme was treated at 0° C. with N-hydroxysuccinimide (127 mg, 1.1 mmol) and dicyclohexylcarbodiimide (227 mg. 1.1 mmol). After 1 hour at 0° C. and 3 hours at room temperature, the reaction mixture was filtered and evaporated to dryness to yield 0.25 g of crude maleimidoacetic acid N-succinimidyl ester.

Maleimidoacetic acid N-succinimidyl ester (0.25 g, 1.0 mmol) was dissolved in 5 ml of acetonitrile, and tris(2-aminoethyl)amine (33 mg, 0.22 mmol) in 200 µl acetonitrile was added dropwise to the solution with stirring. After 30 min. stirring at room temperature, the solution was evaporated to dryness. The residue in 20 ml of ethyl acetate was washed with 5 ml of saturated NaHCO$_3$ solution, 3 ml of 5M NaCl, and dried over anhydrous Na$_2$SO$_4$. After evaporation, the residue was dissolved in 5 ml of triethylammonium ("TEA") formate solution (0.1M, pH 4.1) and purified on a 150 ml Lobar reverse phase C$_{18}$ column eluted with step gradient from 20% MeOH/80% TEA formate to 50% MeOH/50% TEA formate. The yield was 47 mg (38%) (by maleimide titration) of the titled product, tris[2-N-(maleoylglycyl)aminoethyl]amine ("TMG").

Example 3

Preparation Of Antibodies a. Anti-In-EDTA ("CHA")

The antibody herein designated as "CHA" is a monoclonal anti-hapten antibody having specificity for the complex formed between ethylenediaminetetraacetic acid ("EDTA") and the indium (III) ion. For imaging purposes, the $^{111}$In isotope of indium (III) is used. In the present invention, the EDTA derivative, ethanolamine-thioureabenzyl EDTA ("EQTUBE") was used as the chelating agent. The CHA 255 antibody was prepared as follows. Spleen cells from BALB/c mice multiply immunized with the antigen were fused with a variant of the P3.653 myeloma cell line. See Gerhard, *Monoclonal Antibodies*, edited by Kenneth et. al., Plenum Press, New York (1980). The resulting hybridomas were screened by a solid phase second antibody radioimmunoassay for their ability to binding indium aminobenzyl-EDTA (Wang et. al., *Journal of Immunological Methods*, 18, 157 (1977)). Based on their high titers and relatively high affinity as determined by inhibition of binding by unlabeled antigen, a monoclonal antibody designated as CHA 225 was chosen for further study and injected intraperitoneally into BALB/c mice for ascites production. The monoclonal antibodies were purified from mouse ascites by ion-exchange chromatography on DEAE-cellulose as described by Parham et. al., *J. Immunol. Meth.*, 53, 133 (1982). Monoclonal antibody CHA 255 is further described by Reardon, D. T., et. al., *Nature*, 316, p. 265–268 (1985) and Meares et. al., U.S. Pat. No. 4,722,892, issued Feb. 2, 1988, herein incorporated by reference. Hereinafter, the CHA 255 antibody is referred to as "CHA."

b. Anti-Y-DTPA ("CYA")

The antibody designated herein as "CYA" is a monoclonal anti-hapten antibody having specificity for the complex formed between the chelating agent, diethylenetriaminepentaacetic acid ("DTPA"), and the yttrium (III) ion. For therapeutic purpose the $^{90}$Y isotope of yttrium (III) is used. For enhanced pharmaceutical acceptability, the methylthioureabenzyl derivative of DTPA, which is known as methylthioureabenzyldiethylenetriaminepentaacetic acid ("MeTUBD") was used. The CYA 316 antibody (hereinafter "CYA") was prepared using the general techniques described in Reardon, et al., "Antibodies Against Metal Chelates," *Nature*, 316: 265–267 (1985) and in Meares, et al. (U.S. Pat. No. 4,722,892), the latter being incorporated herein by reference.

c. Anti-CEA ("ZCE")

The antibody designated herein as "ZCE" is a monoclonal antibody having specificity for carcinoembryonic antigen. The "ZCE" antibody is commercially available from Jean Pierre Mach, University of Lausanne, Lausanne, Switzerland.

Dr. Mach refers to this antibody as Mab 35 in his publications.

d. Chimeric Anti-CEA ("xCEM")

The antibody designated herein as "xCEM" is a mouse/human chimeric antibody having specificity for carcinoembryonic antigen. The "xCEM" antibody was cloned and expressed according to the procedure taught in Biedler et al., *J. Immunol* 141: pp. 4053–4060 (1988).

e. Chimeric Anti-In-EDTA ("xCHA")

The antibody designated herein as "xCHA" is a mouse human chimeric antibody having specificity for the In-EDTA chelate complex. The "xCHA" antibody was prepared by essentially the same method used for the preparation of "xCEM" above (i.e., *J. Immunol*, 141: pp. 4053–4060 (1988) except that in the preparation of "xCHA" the variable regions from the murine antibody CHA-255 were used instead of the variable regions from the murine antibody CEM-231. The synthesis of xCHA is further described in U.S. patent application Ser. No. 07/274,106, by M. J. Johnson, filed Nov. 17, 1988, now abandoned, and which is herein incorporated by reference. The synthesis of xCHA was also described in a presentation to the 7th International Congress of Immunology, Berlin, Aug. 1, 1989.

EXAMPLE 4

Preparation of Trifunctional Antibody-Like Compounds

Select three different intact antibodies designated herein as $Ab_1$, $Ab_2$, and $Ab_3$, which have the desired specificities and affinity constants. The antibodies are individually digested with pepsin using conventional techniques, such as the procedure described in Example 5(a) herein, yielding $F(ab')_2$ fragments designated as $F_1(ab')_2$, $F_2(ab')_2$, and $F_3(ab')_2$, respectively.

The $F(ab')_2$ fragment derived from each of the three antibodies is reduced with cysteine (or other similar reducing agent) to its respective Fab' fragments, i.e., $F_1ab'$, $F_2ab'$, and $F_3ab'$, using a conventional procedure, such as that described in Example 5(b).

The three reduced Fab' fragments are selectively coupled together according to the following procedure to form a trifunctional antibody-like compound via a trifunctional coupling agent. For purpose of this example, tris[2-N-(maleoylglycyl)aminoethyl]amine ("TMG") from Example 2 is the trifunctional coupling agent that is utilized. Procedurally, $F_1ab'$—SH is added to a 30-fold molar excess of TMG dissolved in DMF, preferably pH 5-7. The reaction mixture is incubated at room temperature for 10 minutes. Thereafter, the reaction mixture is applied to a P-6 column (Biorad Laboratories, Richmond, Calif.) that has been pre-equilibrated and which is eluted with citrate buffered saline (50 mM ammonium [or sodium] citrate, 100 mM NaCl, 1 mM DTPA, pH 6.3). Elution of the protein fraction from the column is determined by monitoring the absorbance of the eluate at 280 nm ($A_{280}$). The protein fraction from the P-6 column (Biorad Laboratories, Richmond, Calif.) contains the purified $F_1ab'$-TMG which contains at least one maleimide moiety capable of coupling to a second reduced Fab' fragment.

The eluent containing the $F_1ab'$-TMG is added dropwise to the second reduced Fab' fragment, $F_2ab'SH$, which is dissolved in the same citrate buffer as used to elute the P-6 column. This second coupling reaction is allowed to proceed for 3 hours at room temperature. Thereafter, the sulfhydryls remaining on the $F_2ab'SH$ molecules are protected by a reversible protecting agent, such as DTNB (5,5'-dithio-bis-(2-nitrobenzoic acid)). Protection is accomplished by first adding sufficient DTNB to achieve a final concentration of approximately 1 mM in the citrate buffered saline (50 mM ammonium citrate, 100 mM NaCl, 1 mM DTPA, pH 6.3) which contains the $F_1ab'$-TMG-$F_2ab'SH$. Thereafter, the reaction mixture is incubated for 10 minutes at room temperature. The resulting protected intermediate, $F_1ab'$-TMG-$F_2ab'$-S-blocking agent, is purified by high pressure liquid chromatography (HPLC), using a matrix comprising either Fast Flow S (Pharmacia, Piscataway, N.J.) or TSK-GEL SP-TOYOPEARL® 650s (Tosoh Corp., Japan) or by preparative gel filtration, such as on a column containing Sephadex® G-150 brand superfine resin (Pharmacia, Piscataway, N.J.).

Once purified, the protected intermediate, is deblocked in borate buffered saline (50 mM sodium borate, 50 mM NaCl, pH 8.2) to which is added a molar excess of cysteine (e.g., 1 mM), DTT (dithiothreitol), or an effectively equivalent amount of a similar reducing agent. The deblocked and reduced bifunctional intermediate is further purified by applying the reaction mixture to a P-6 column (Biorad Laboratories, Richmond, Calif.) which has been pre-equilibrated with and which is eluted with the just described citrate buffered saline, pH 6.3. The reduced bifunctional intermediate, $F_1ab'$-TMG-$F_2ab'$-SH, is now ready for coupling to a derivatized third Fab' fragment.

The third Fab' fragment is derivatized by being added to a 30-fold molar excess of TMG (or other trivalent coupling agent such as described herein dissolved in an organic solvent (DMF). The reaction mixture is incubated at room temperature for 10 minutes. Thereafter, the $F_2ab'$-TMG in the reaction mixture is purified by applying the reaction mixture to a P-6 column (Biorad Laboratories, Richmond, Calif.) that has been pre-equilibrated with and which is eluted with the described citrate buffered saline, pH 6.3.

Final coupling to produce the trivalent antibody-like compound of the present invention is accomplished by adding $F_3ab'$-TMG to a solution of the above described citrate buffered saline (pH 6.3) containing the $F_1ab'$—TMG—$F_2ab'SH$ and then allowing the reaction to proceed for 3 hours at room temperature. Thereafter, the reaction is stopped, such as by the addition of the alkylating agent, N-ethylmaleimide, to the reaction mixture. Purification of the trivalent antibody-like compound is accomplished by HPLC, or preparative gel filtration (e.g., Pharmacia's SEPHAROSE® brand G-150 superfine resin), which techniques are well known to those of ordinary skill in the art.

Example 5

Preparation Of The Trifunctional Antibody-Like Compound: CHA-BMP-CYA-BMP-ZCE

Three different antibodies were the source of the Fab' fragments that were coupled by two trivalent coupling agents to form a trifunctional antibody-like compound. In this example, the monoclonal antibody is designated as "CHA," "CYA," and "ZCE" were prepared or obtained as referenced in Example 3 herein.

(a) Preparation of $F(ab')_2$ Fragments From Intact Antibody

The $F(ab')_2$ fragments of CHA, CYA, and ZCE, which are designated as CHA—$F(ab')_2$, CYA—$F(ab')_2$, and ZCE—$F(ab')_2$ respectively, were prepared by individually digesting the respective antibody with pepsin according to the following procedure.

Antibody solutions, having an antibody concentration of 5-15 mg/ml as determined by their absorbance at 280 nm ("$A_{280}$"), were dialyzed in acetate buffered saline (0.1M sodium acetate, 0.1M NaCl, pH 4.1) overnight at 4° C. Thereafter, a concentrated pepsin solution, i.e., a solution containing pepsin that was equivalent to 2% of the antibody mass, was added to the dialyzed solution. The reaction mixture was then incubated from 4-48 hours at 37° C. The reaction was terminated by adjusting the pH to approximately 8 with $NaHCO_3$. The $F(ab')_2$ fragments were purified by a variety of techniques, including gel filtration on a SEPHADEX® G-150 column (Pharmacia, Piscataway, N.J.); high pressure liquid chromatography, using as a matrix either Fast Flow S (Pharmacia) or TSK-GEL SP-TOYOPEARL® 650s cation exchange resin (Tosoh Corp., Japan). After isolation, the $F(ab')_2$ fragment was dialyzed in borate buffered saline (50 mM sodium borate, 50 mM NaCl, pH 8.2). The dialyzed solutions containing the respective F(ab')$_2$ fragments were used in the subsequent reduction steps.

(b) Reduction of CYA-F(ab')$_2$ to CYA-Fab'-SH

To 1.0 mL of borate buffered saline (50 mM sodium borate, 50 mM NaCl, pH 8.2) containing 8.1 mg/ml of CYA$_{316}$F(ab')$_2$, was added 2 μl of 0.5M diethylenetriaminepentaacetic acid (DTPA) and 40 μl of 0.5M cysteine. The reaction mixture was allowed to proceed for 10 minutes at 37° C. Thereafter, the reaction mixture was applied to a 15 mL P-6 column (Biorad Laboratories, Richmond, Calif. 94804) that had been pre-equilibrated and eluted with citrate buffered saline (50 mM ammonium citrate, 100 mM NaCl, 1 mM DTPA, pH 6.3). A 3.0 ml protein containing fraction was collected from the column, which based upon its absorbances at 280 nm (A$_{280}$) had a protein (reduced Fab') concentration of 48 μM. The concentration of free sulfhydryl groups in the protein fraction was determined to be 118 μM by adding excess 5,5'-dithiobis-(2-nitrobenzoic acid), i.e., "DTNB, " borate buffered saline to an aliquot of the reaction mixture and measuring the absorbance difference at 412 nm between the aliquot containing DTNB and a blank. Thereafter, the ratio of free sulfhydryl groups per Fab' fragment was calculated to be 2.5:1.

(c) Reduction of CHA-F(ab')$_2$ to CHA-Fab'SH

A 5 ml of aliquot of a final dialyzed solution from step (a) above, which contained 10 mg/ml CHA-F(ab')$_2$, was reduced and purified on a P-6 column according to the procedure in step (b) above. Upon elution of the P-6 column (Biorad Laboratories, Richmond, Calif.), a 12 ml protein fraction was collected. Based upon the absorbance of the fraction at 280 nm, the concentration of the F(ab') fragment was 86 μM. The sulfhydryl concentration of the protein fraction was determined to be 163 μM using 5,5'-dithiobis-(2-nitrobenzoic acid) ("DTNB") and measuring the absorbance differences at 412 nm. The molar ratio of sulfhydryl groups to Fab' fragments for CHA-Fab'SH was calculated to be 1.9:1.

(d) BMP Derivatization of CHA-Fab'SH

To 1 ml of a 50:50 solution of DMF/H$_2$O was added 13 mg of N,N'-bis(3-maleimidopropionyl)-2-hydroxy-1,3-propanediamine (hereinafter "BMP") which is commercially available from Sigma Chemical Co., St. Louis, MO. After dissolution of the BMP, 12 ml of the 86 μM protein fraction from step (c) above, which contained CHA-Fab'SH, was added to the BMP solution. The reaction mixture was allowed to stand for 10 minutes at room temperature. Thereafter, the reaction mixture was applied to a 200 ml P-6 column (Biorad Laboratories, Richmond, Calif.) and a 27 ml protein fraction, which contained the CHA-Fab'BMP, was collected. The A$_{280}$ indicated the CHA-Fab'BMP concentration to be 33 μM.

Using back titration, the maleimide content of the protein fraction was determined. Specifically, to a 300 μl aliquot of the 27 ml protein fraction from 5(d) above was added 20 μl of 1.0 mM cysteine. The a mixture was allowed to stand at room temperature for 5 minutes. Thereafter, 10 μl of 10 mM 5,5'-dithiobis-(2-nitrobenzoic acid) i.e., DTNB, and 670 μl of borate buffered saline (50 mM ammonium borate, 50 mM NaCl, pH 8.2) were added to the reaction mixture. The reaction mixture was spectrophotometrically measured at 412 nm, compared to a standard without Fab'-BMP, and the difference between the two was used to determine maleimide content, which in this case was 33 μM. The number of maleimide moieties available per CHA-Fab' was calculated as 1.0.

(e) Reduction of ZCE-F(ab')$_2$ to ZCE-Fab'SH

A commercially available monoclonal antibody to CEA, which was licensed from Jean Pierre Mach, University of Lausanne, Lausanne, Switzerland, and designated herein as ZCE, was digested with pepsin according to the procedure in Example 5(a) above to produce its corresponding F(ab')$_2$ fragment, designated as ZCE-F(ab')$_2$.

To a 4 ml aliquot of final dialyzed solution from the pepsin digestion above, which contained 10 mg/ml ZCE-F(ab')$_2$, was added 10 μl of 0.5M DTPA and the reaction mixture was allowed to incubate for 10 minutes at 37° C. Thereafter, 160 μl of 0.5M cysteine was added and the reaction mixture was incubated at 37° C. for a further 10 minutes. The reaction mixture was then applied to a 40 ml P-6 column (Biorad Laboratories, Richmond, Calif. ) that was pre-equilibrated and eluted with citrate buffered saline (50 mM ammonium citrate, 100 mM NaCl, 1 mM DTPA, pH 6.3). A 11.3 ml protein fraction was collected, which based upon its absorbance at 280 nm (A$_{280}$) was 79 μM in the reduced protein. The sulfhydryl content of the protein fraction was determined to be 149 μM, using DTNB as described in Example 5(b) above. The ratio of sulfhydryl groups per ZCE-Fab' fragment was calculated to be 1.9:1. The resultant fragment is designated ZCE-Fab'SH.

(f) Conjugation of CHA-Fab'BMP to ZCE-Fab'SH

To the 79 μM solution of ZCE-Fab'SH from step (e) above was added in a dropwise fashion an amount of the 33 μM solution of CHA-Fab'BMP sufficient to provide a 1:1 ratio of sulfhydryl group to reactive maleimide. The reaction mixture was allowed to stand overnight at 4° C. Thereafter, any unreacted sulfhydryl was blocked by the addition of 16 mg of DTNB to the reaction mixture, thereby providing a concentration of approximately 1 mM DTNB.

The resultant bifunctional antibody-like compound, designated as CHA-BMP-ZCE, was purified from the reaction mixture by a variety of techniques including high pressure liquid chromatography (HPLC) using as matrices either Fast Flow S (Pharmacia) or TSK-GEL SP-TOYOPEARL® 650S cation exchange resin (Tosoh Corp., Japan); and by gel filtration on a SEPHADEX® G-150 column (Pharmacia, Piscataway, N.J.). Those of ordinary skill in the art are familiar with protein purification via the techniques of HPLC, and gel filtration.

(g) Deblocking CHA-BMP-ZCE To Form CHA-BMP-ZCE-SH

To a 2.5 ml aliquot containing 3.9 mg/ml of the purified blocked CHA-BMP-ZCE in borate buffered saline (50 mM sodium borate, 50 mM NaCl, pH 8.2) was added 5 μl of 0.5M diethylenetriaminepentaacetic acid ("DTPA"). The reaction mixture was incubated for 15 minutes at 37° C. followed by the subsequent addition of 100 μl of 0.5M cysteine. The reaction mixture was further incubated for 10 minutes at 37° C., which effected deblocking. Thereafter, the reaction mixture was applied to a P-6 column (Biorad Laboratories, Richmond, Calif.) that had been pre-equilibrated and which was eluted with citrate buffered saline (50 mM ammonium citrate, 100 mM NaCl, 1 mM DTPA, pH 6.3). A 5.8 ml protein fraction was collected, which based upon its absorbance at 280 nm (A$_{280}$), had a 15 μM protein (reduced bifunctional antibody) concentration. The sulfhydryl concentration of the protein fraction was subsequently determined, according to the procedure in Example 5(a) above.

(h) Coupling CYA-BMP With CHA-BMP-ZCE-SH To Form CHA-BMP-ZCE-BMP-CYA

To 5.5 ml of the citrate buffered saline solution that was 15 μM in CHA-BMP-ZCE-SH (from Example 5(g)) was added an equimolar amount of CYA-BMP (prepared as described in Steps (c) and (d) similarly dissolved in citrate buffered saline (50 mM sodium citrate, 100 mM NaCl, pH 6.3). The reaction was allowed to proceed for 3 hours at room temperature and then was terminated with N-ethylmaleimide as described in Example 4 herein. The resultant trifunctional antibody-like compound, designated as CHA-BMP-ZCE-BMP-CYA, was purified by gel filtration on SEPHADEX® G-150 (Pharmacia, Piscatway, N.J.). Fractions 38-43 were collected and pooled to yield 3.2 ml of a solution containing 0.66 mg/ml of the purified product. A 2.0 ml aliquot of the pooled fractions was then dialyzed overnight in 0.17M sodium acetate, pH 4.5, for subsequent HPLC purification on a Mono S matrix (Pharmacia).

The uncorrected binding capacity for the In-EOTUBE complex by the CHA-BMP-ZCE-BMP-CYA in the 0.66 mg/ml pooled fraction was determined to be 76% of theoretical capacity. The control for the same run exhibited a binding capacity of 4%. The binding capacity for CYA was 82% of the theoretical value.

Example 6

Synthesis Of The Trivalent Antibody-Like Compound: xCEM-TMG-xCHA-TMG-xCEM (a) Digestion of "xCHA" and "xCEM" to xCHA-F(ab')$_2$ and xCEM-F(ab')$_2$ Respectively.

Intact chimeric monoclonal antibody to the In-EDTA complex is designated herein as "xCHA." Intact chimeric monoclonal antibody to CEA is designated herein as "xCEM." The preparation of these antibodies was as referenced in Example 3 herein. Intact xCHA and xCEM antibodies were individually digested to their respective F(ab')$_2$ fragments by incubating each with 3% pepsin (pepsin:antibody) at 37° C. for 5 hours in acetate buffered saline (100 mM sodium acetate, 100 mM sodium chloride, pH 4.1). The digests were terminated by neutralization of the pH. Thereafter the digests were dialyzed in borate buffered saline (50 mM sodium borate, 100 mM sodium chloride, pH 8.2) to provide the corresponding F(ab')$_2$ fragments designated as xCHA-F(ab')$_2$ and xCEM-F(ab')$_2$ respectively.

(b) Reduction of xCEM-F(ab')$_2$ to xCEM-Fab'SH

To 6 ml of xCEM-F(ab')$_2$ (17 mg/ml) obtained from Example 6(a) above was added 2.0 ml of borate buffered saline (50 mM sodium borate, 100 mM sodium chloride, pH 8.2) and 16 μl of 0.5M diethylenetriaminepentaacetic acid ("DTPA"), i.e., until a final DTPA concentration of 1 mM. The reaction mixture was incubated at 37° C. for 10 minutes, followed by the addition of 360 μl of 0.5M cysteine, and a further incubation for 10 minutes at 37° C. The cysteine was removed by gel filtration on a 2.5×19 cm P-6 DG column (Biorad Laboratories, Richmond, Calif. 94804) that had been pre-equilibrated with and which was eluted with citrate buffered saline (50 mM ammonium citrate, 100 mM NaCl, 1 mM DTPA, pH 6.3). Upon elution, a 19.6 ml protein fraction was collected, which based upon its absorbance at 280 nm (A$_{280}$) was 90 μM in the reduced Fab' fragment-xCEM-Fab'SH. The free sulfhydryl concentration of the protein fraction was determined to be 159 μM by reaction with DTNB as described in Example 5(b) herein. The ratio of free sulfhydryl per reduced Fab' fragment was calculated to be 1.8:1.

(c) Derivatization of xCEM-Fab'SH with TMG

The reduced Fab' fragment, xCEM-Fab'SH, was derivatized with a 30 fold molar excess of tris(2-maleoylglycylaminoethyl)amine ("TMG"). In particular, 19.5 ml of xCEM-Fab'SH (1.8 μmoles) in citrate buffered saline from Example 6(b) above was added with stirring to 176 μl of 314 mM TMG (53 μmoles) in DMF. After 10 minutes at 23° C., excess TMG was removed on a 2.5×45 cm P-6 DG column (Biorad Laboratories) that was pre-equilibrated and eluted with citrate buffered saline (50 mM ammonium citrate, 100 mM NaCl, 1 mM DTPA, pH 6.3). A 26.8 ml protein fraction was collected, which based upon its absorbance at 280 nm (A$_{280}$) contained 3.3 mg/ml or was 67 μM in the derivatized fragment-xCEM-Fab'-TMG. The determination of active maleimides by back titration (per Example 5(d)) indicated 1.16 active maleimides per Fab' fragment.

(d) Reduction of xCHA-F(ab')$_2$ To xCHA-Fab'SH

A 2.7 ml aliquot of xCHA-F(ab')$_2$ (9.2 mg/ml) was incubated with 1 mM DTPA for 10 minutes at 37° C. To this reaction mixture was then added 6 μl of 0.5M dithiothreitol ("DTT") and the reaction mixture was incubated at 37° C. for a further 10 minutes. The DTT was removed by gel filtration on a 1.5×25 cm P-6 DG column (Biorad Laboratories) that was pre-equilibrated and eluted with citrate buffered saline (50 mM ammonium citrate, 100 mM NaCl, 1 mM DTPA, pH 6.3). A 7.6 ml protein fraction was collected, which based upon its absorbance at 280 nm (A$_{280}$) was 59 μM in the desired xCHA-Fab'SH. The free sulfhydryl concentration of the fraction was determined to be 236 μM. The ratio of free sulfhydryl groups per reduced Fab' fragment was calculated to be 4.7:1.

(e) Coupling Between xCHA-Fab'SH and xCEM-Fab'TMG

To 7.5 ml of xCHA-Fab'SH from 6(d) above was added 26.2 ml of xCEM-Fab'-TMG from 6(c) above and the reaction mixture was incubated at 23° C. for 100 minutes. The reaction was terminated by the addition of 34 μl of 1M N-ethylmaleimide, an alkylating agent. The reaction mixture was then concentrated to 12 ml by ultrafiltration. The concentrated reaction mixture was purified by gel filtration on a 2.6×96 cm G-150 superfine column (Pharmacia, Piscataway, N.J.). The flow rate was approximately 0.2 ml/min. The A$_{280}$ trace of the elution pattern indicated 3 major products. The desired trivalent antibody-like compound, designated herein as xCEM-TMG-xCHA-TMG-xCEM, was found as the middle product in fractions 38-41. The identity of the xCEM-TMG-xCHA-TMG-xCEM was confirmed by high pressure liquid chromatography (HPLC) gel filtration and by sodium dodecyl sulfate-polyacrylamide gel electrophoresis (SDS-PAGE, 7.5% acrylamide).

EXAMPLE 7

Antigen Binding Capacity Of The Trifunctional Antibody-Like Compound: CHA-ZCE-CYA The antigen binding capacities of the trifunctional antibody-like compound CHA-ZCE-CYA were determined for both the $^{90}$Yttrium-MeTUBD complex (i.e. a therapeutic agent) and for the $^{111}$Indium-EOTUBE complex (i.e. a diagnostic agent) using techniques well known to those of ordinary skill in the art. In particular, trace labeled $^{90}$Y-MeTUBD was prepared by combining a known concentration of Y-MeTUBD with a known concentration of $^{90}$Y-MeTUBD. Likewise a known concentration of In-EOTUBE was combined with a known concentration of $^{111}$In-EOTUBE. The % binding by CYA and CHA for each of the trace labeled complexes was then determined.

The results of these assays indicate that CYA moiety of the trifunctional antibody-like compound, CHA-ZCE-CYA, binds an amount of Yttrium-MeTUBD corresponding to 82% of its maximum theoretical capacity. Similarly, an assay for the binding capacity of the CHA moiety of CHA-ZCE-CYA for the Indium-EOTUBE complex revealed a binding capacity of 76% of its maximum theoretical capacity. It was further demonstrated in similar assays that the CHA moiety was specific for the Indium-EOTUBE complex, since CHA cross-bound only 1% of the Y-MeTUBD. Likewise, the CYA binding was specific to the Yttrium-MeTUBD complex, with only 4% of Indium-EOTUBE being taken up by the control.

What is claimed is:

1. A pharmaceutical composition comprising:
(a) a compound of the formula: $F_1ab'$—L—$F_2ab'$—L—$F_3ab'$ wherein $F_1ab'$, $F_2ab'$, and $F_3ab'$ are three different Fab'-like fragments and wherein L is a bis-succinimidyl and/or a tris-succinimidyl moiety that is the same or different, each L covalently cross-linking two of said three different Fab'-like fragments, said three different and cross-linked Fab'-like fragments substantially retaining their antigen binding activity; and
(b) one or more pharmaceutically acceptable carriers.

2. The pharmaceutical composition of claim 1 wherein any one of $F_1ab'$, $F_2ab'$ or $F_3ab'$ is an Fab'-like fragment of a monoclonal antibody that is capable of forming a binding pair in vivo with a physiologically compatible chelate complex comprising a chelating agent and a beta emitting metal ion.

3. The pharmaceutical composition of claim 2 wherein said physiologically compatible chelate complex has a dissociation constant of $10^{-16}$ to $10^{-20}$.

4. The pharmaceutical composition of claim 3 wherein the chelating agent is selected from the group consisting of ethylenediaminetetraacetic acid ("EDTA"), ethanolaminethioureabenzyl-EDTA ("EOTUBE"), diethylenetriaminepentaacetic acid ("DTPA"), methylthioureabenzyl DTPA ("MeTUBD"), 1,4,7,10-tetrazacyclododecane-N',N'',N''',N''''-tetraacetic acid ("DOTA"), L-aminobenzyl-EDTA, 1,5,9,13-tetraazacyclohexadecane-N, N', N'', N'''-tetraacetic acid ("HETA"), 1,4,7,10-tetraazacyclotridecane-N, N', N'', N'''-tetraacetic acid, and 1,4,8,11-tetraazacyclotetradecane-N, N', N'', N'''-tetraacetic acid ("TETA").

5. The pharmaceutical composition of claim 4 wherein the beta emitting metal ion is selected from the group consisting of $^{67}$Cu, $^{186}$Rh, $^{188}$Rh, $^{189}$Rh, $^{153}$Sm and $^{90}$Y, in ionic form.

6. The pharmaceutical composition of claim 5 wherein the physiologically compatible chelate complex is $^{90}$Y-MeTUBD, $^{90}$Y-DTPA, or $^{90}$Y-DOTA.

7. The pharmaceutical composition of claim 6 wherein each L is a trissuccinimidyl moiety.

8. The pharmaceutical composition of claim 7 wherein a second one of $F_1ab'$, $F_2ab'$ or $F_3ab'$ is capable of forming a binding pair in vivo with a second physiologically compatible chelate complex, said second physiologically compatible complex comprising a second chelating agent and a gamma emitting metal ion.

9. The pharmaceutical composition of claim 8 wherein said second chelating agent is selected from the group consisting of EDTA, EOTUBE, DTPA, MeTUBD, DOTA, HETA, TRITA and TETA.

10. The pharmaceutical composition of claim 9 wherein the gamma emitting metal ion is selected from the group consisting of $^{111}$In, $^{113m}$In, $^{67}$Ga, $^{68}$Ga, $^{99m}$Tc, $^{51}$Cr, $^{197}$Hg, $^{203}$Hg, $^{169}$Yb, $^{85}$Sr., and $^{87}$Sr, in ionic form.

11. The pharmaceutical composition of claim 10 wherein a third one of $F_1ab'$, $F_2ab'$ or $F_3ab'$ has specificity for an antigen expressed by a cell.

12. The pharmaceutical composition of claim 11 in unit dosage form.

13. A composition comprising a compound of the formula:

$$F_1ab'\text{—}L\text{—}F_2ab'\text{—}L\text{—}F_3ab' \qquad (I)$$

wherein $F_1ab'$, $F_2ab'$ and $F_3ab'$ are three different Fab'-like fragments; and
wherein L is a bis-succinimidyl and/or a tris-succinimidyl moiety that is the same or different, each L covalently cross-linking two of said three different and cross-linked Fab'-like fragments, said three different Fab'-like fragments substantially retaining their antigen binding activity;
whereby the compound of Formula I is capable of forming binding pairs with three different epitopes.

14. The composition of claim 13 wherein each L is a tris-succinimidyl moiety.

15. The composition of claim 14 wherein one of said three different Fab'-like fragments is capable of forming a binding pair with a first physiologically compatible chelate complex comprising a first chelating agent and a first metal ion, said first physiologically compatible chelate complex being characterized by having a dissociation constant of $10^{-16}$ to $10^{-20}$.

16. The composition of claim 15 wherein the first chelating agent is selected from the group consisting of EDTA, DTPA, MeTUBD, DOTA, HETA, TRITA, and TETA.

17. The composition of claim 16 wherein the first metal ion is selected from the group consisting of $^{111}$In, $^{113m}$In, $^{67}$Ga, $^{68}$Ga, $^{99m}$Tc, $^{51}$Cr, $^{197}$Hg, $^{203}$Hg, $^{169}$Yb, $^{85}$Sr, and $^{87}$Sr, in ionic form.

18. The composition of claim 17 wherein the first metal ion is $^{111}$In(III).

19. The composition of claim 18, wherein a second one of said three different Fab'-like fragments is capable of forming a binding pair with a second physiological compatible chelate complex comprising, a second chelating agent and a second metal ion, said second physiologically compatible chelate complex being characterized by having a dissociation constant of $10^{-16}$ to $10^{-20}$.

20. The composition of claim 19 wherein the second chelating agent is selected from the group consisting of EDTA, EQTUBE, DTPA, MeTUBD, DOTA, HETA, TRITA and TETA.

21. The composition of claim 20 wherein the second metal ion is selected from the group consisting of $^{67}$Cu, $^{186}$Rh, $^{188}$Rh, $^{189}$Rh, $^{153}$Sm and $^{90}$Y, in ionic form.

22. The composition of claim 21 wherein the second metal ion is $^{90}$Y in ionic form and the second chelating agent is DTPA or MeTUBD.

23. The composition of claim 22 wherein a third one of said three different Fab'-like fragments is capable of binding to an antigen expressed by a cell.

24. The composition of claim 23 wherein each of F$_1$ab', and F$_2$ab', and F$_3$ab' is an Fab'-like fragment from a monoclonal antibody.

25. The composition of claim 24 wherein the antigen expressed by a cell is selected from the group consisting of alphafetoprotein, c-erbB-2, cancer antigen 15-3 ("CA 15-3"), CA 19-9, CA 125, CA 195, CA 549, carcinoembryonic antigen ("CEA"), cathepsin D ("cath D"), cytokeratins, Du-PAN-2, Epidermal Growth Factor Receptor ("EGF-R"), estrogen receptor, C-myc, N-myc, prostate specific antigen (PSA), ras, tumor associated antigen-72 ("TAG-72"), tumor associated antigen-4 ("TA-4") and the KS ¼ antigen.

26. The composition of claim 25 wherein the cellular antigen is CEA.

* * * * *